US009506935B2

(12) United States Patent
Huet et al.

(10) Patent No.: US 9,506,935 B2
(45) Date of Patent: Nov. 29, 2016

(54) METHOD AND SYSTEM FOR ESTIMATING THE QUANTITY OF AN ANALYTE CONTAINED IN A LIQUID

(71) Applicant: Commissariat à l'énergie atomique et aux énergies alternatives, Paris (FR)

(72) Inventors: Maxime Huet, Grenoble (FR); Vincent Poher, Guines (FR); Myriam-Laure Cubizolles, Corenc (FR); Patrick Pouteau, Meylan (FR); Cédric Allier, Grenoble (FR); Johanna Spiaczka, Roissard (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/560,623

(22) Filed: Dec. 4, 2014

(65) Prior Publication Data
US 2015/0160244 A1  Jun. 11, 2015

Related U.S. Application Data

(63) Continuation-in-part of application No. 13/905,727, filed on May 30, 2013.

(30) Foreign Application Priority Data

Jun. 1, 2012 (FR) ..................... 12 55115

(51) Int. Cl.
G06K 9/00 (2006.01)
G01N 33/80 (2006.01)
(Continued)

(52) U.S. Cl.
CPC .......... *G01N 33/80* (2013.01); *G01N 15/1434* (2013.01); *G01N 15/1436* (2013.01);
(Continued)

(58) Field of Classification Search
CPC ..................... G01N 15/1434; G01N 15/1436; G01N 2015/0073; G01N 2015/1075; G01N 2015/1454; G01N 2021/825; G01N 21/82; G01N 33/4905; G01N 33/80
See application file for complete search history.

(56) References Cited

U.S. PATENT DOCUMENTS

2003/0096324 A1   5/2003   Matveev et al.
2003/0113925 A1   6/2003   Gordon et al.
(Continued)

OTHER PUBLICATIONS

French Search Report for FR 12 55115 dated Feb. 21, 2013.
(Continued)

*Primary Examiner* — Tom Y Lu
(74) *Attorney, Agent, or Firm* — B. Aaron Schulman, Esq.; Stites & Harbison, PLLC

(57) ABSTRACT

This method for estimating the quantity of an analyte contained in a liquid includes the following steps:
  introducing the liquid into a fluid chamber;
  mixing the liquid with a bi-specific reagent, the bi-specific reagent being configured for grafting on both a particle and an analyte present in the liquid;
  lighting the fluid chamber using an excitation beam emitted by a light source, the beam extending through the fluid chamber;
  acquiring at least one image using a matrix photodetector, the image being formed by radiation transmitted by the lighted fluid chamber; and
  estimating, from at least one acquired image, the quantity of said analyte in the liquid.

16 Claims, 22 Drawing Sheets

(51) Int. Cl.
  *G01N 15/14* (2006.01)
  *G01N 21/82* (2006.01)
  *G01N 33/555* (2006.01)
  G01N 15/00 (2006.01)
  G01N 33/49 (2006.01)
  G01N 15/10 (2006.01)

(52) U.S. Cl.
  CPC ............ *G01N21/82* (2013.01); *G01N 33/555* (2013.01); *G01N 33/4905* (2013.01); *G01N 2015/0073* (2013.01); *G01N 2015/1075* (2013.01); *G01N 2015/1454* (2013.01); *G01N 2021/825* (2013.01); *G01N 2333/75* (2013.01)

(56) References Cited

U.S. PATENT DOCUMENTS

| 2009/0274348 A1 | 11/2009 | Jakubowicz et al. |
| 2010/0248278 A1 | 9/2010 | Pouteau et al. |
| 2010/0260391 A1 | 10/2010 | Ichitani et al. |
| 2010/0267066 A1 | 10/2010 | Hosokawa et al. |
| 2011/0136165 A1 | 6/2011 | Vojnovic et al. |
| 2012/0309636 A1* | 12/2012 | Gibbons ............ H04N 5/23222 506/9 |

OTHER PUBLICATIONS

Dan Chicea:"Results of sediment motion visualization by a modified LASCA technique", Proceedings of SPIE, International Society for Optical Engineering, US, vol. 6785, (Jan. 1, 2007) pp. 678510.

Kalchenko V et al: "In vivo dynamic light scattering imaging of blood coagulation", Journal of Biomedical Optics, SPIE-International Society for Optical Engineering, US, vol. 12, No. 5, (Sep. 12, 2007) pp. 52002-1.

Seemantini K Nadkarni et al: "Characterization of Atherosclerotic Plaques by Laser Speckle Imaging", Circulation, Lippincott Williams & Wilkins, US, vol. 112,(Jan. 1, 2005) pp. 885-892.

Piederriere Y et al: "Evaluation of blood plasma coagulation dynamics by speckle analysis", Journal of Biomedical Optics, SPIE—International Society for Optical Engineering, US, vol. 9, No. 2, (Mar. 1, 2004), pp. 408-412.

European Office Action dated Sep. 16, 2013 in corresponding European Application No. 13 169 989.4.

* cited by examiner

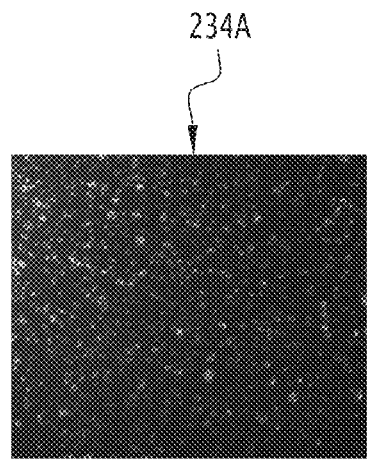
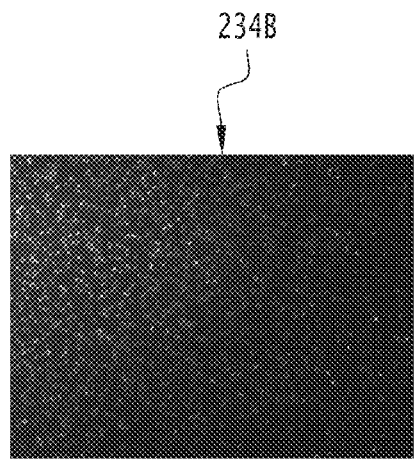
FIG.40        FIG.41
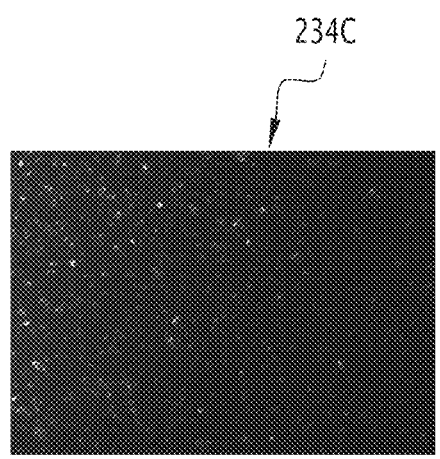
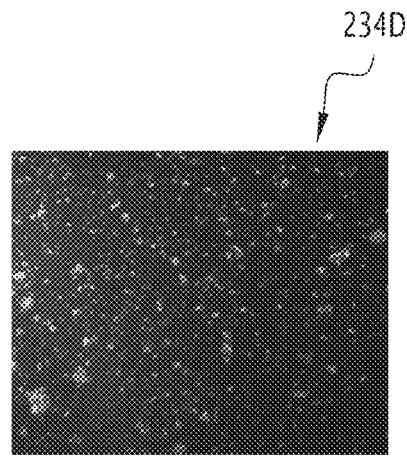
FIG.42        FIG.43
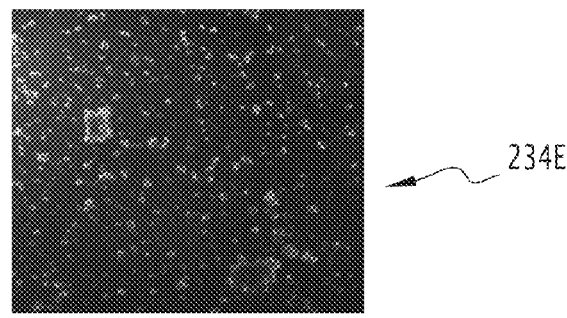
FIG.44

METHOD AND SYSTEM FOR ESTIMATING THE QUANTITY OF AN ANALYTE CONTAINED IN A LIQUID

CROSS-REFERENCE TO RELATED APPLICATIONS

This application is a Continuation-In-Part of U.S. patent application Ser. No. 13/905,727, filed May 30, 2013, said application hereby incorporated by reference in its entirety.

BACKGROUND OF THE INVENTION

The present invention concerns a method for estimating the quantity of an analyte contained in a liquid.

The invention also relates to a system for estimating the quantity of an analyte contained in the liquid.

The invention in particular relates to the field of lensless imaging of the beam lighting the fluid chamber, in order to characterize a liquid, such as blood.

The invention in particular applies to the estimation of the quantity of a D-dimer contained in the liquid. D-dimer is a small protein fragment present in the blood after a blood clot is degraded by fibrinolysis. D-dimer is therefore a fibrin degradation product.

D-dimer concentration is usually determined by a blood test to help diagnose thrombosis, in particular for patients with suspected thrombotic disorders. A positive result may indicate thrombosis but does not rule out other potential causes. Therefore, this test is essentially used to exclude thromboembolic disease where the probability is low, and in addition, to diagnose a blood disorder disseminated intravascular coagulation.

Known from document EP 2,233,923 A1 is a characterization method and system for characterizing a variation in the speed of particles or agglomeration of particles, the particles, such as blood particles, being contained in a liquid. The described method aims to characterize the coagulation or sedimentation dynamics of a fluid containing blood. The system for implementing this method comprises a fluid chamber receiving liquid, a spatially coherent light source capable of emitting a lighting laser beam. The laser beam extends in a longitudinal direction towards the fluid chamber.

The system also comprises an image sensor, such as a matrix sensor of the CCD (Charged-Coupled Device) or CMOS (Complementary Metal Oxide Semiconductor) type, arranged to make it possible to acquire a temporal series of images of an optical granularity pattern created by the interaction between the particles contained in the chamber and the laser beam. The characterization system also comprises a processing unit for processing said temporal series of images.

The distance between the fluid chamber and the image sensor in the longitudinal direction is several centimeters or tens of centimeters. The laser beam emitted by the spatially coherent light source has a surface comprised between 10 $\mu m^2$ and several $mm^2$ along a plane perpendicular to the longitudinal direction and passing through the fluid chamber.

Such a system and method make it possible to effectively characterize the coagulation or sedimentation dynamics of the blood contained in the liquid.

However, such a system is relatively bulky. Furthermore, it makes it possible to observe the coagulation phenomenon only in a relatively small volume of the fluid chamber. In addition, this system is not adapted for estimating the quantity of an analyte contained in a liquid.

SUMMARY OF THE INVENTION

The aim of the invention is therefore to propose an estimation method and system for estimating the quantity of an analyte contained in the liquid, and furthermore making it possible to observe a larger volume of liquid while limiting the bulk of the estimation system.

To that end, the invention relates to an estimation method for estimating the quantity of an analyte contained in a liquid, wherein the method includes the following steps:
  introducing the liquid into a fluid chamber;
  mixing the liquid with a bi-specific reagent, the bi-specific reagent being configured for grafting on both a particle and an analyte present in the liquid;
  lighting the fluid chamber using an excitation beam emitted by a light source, the beam extending through the fluid chamber;
  acquiring at least one image using a matrix photodetector, the image being formed by radiation transmitted by the lighted fluid chamber; and
  estimating, from at least one acquired image, the quantity of said analyte in the liquid.

According to other advantageous aspects of the invention, the estimation method comprises one or more of the following features, considered alone or according to any technically possible combinations:
  the liquid includes blood, and the bi-specific reagent is configured for grafting on both a blood particle and an analyte present in the liquid;
  the blood particle is a red blood cell, the bi-specific reagent being configured for grafting on both the red blood cell and the analyte;
  the analyte is a D-dimer;
  the method further includes a step of calculating an indicator for each acquired image, the indicator being representative of the intensity of the pixels of the image in a predetermined region of the image; and during the estimation step, the quantity of said analyte is estimated according to said indicator;
  during the calculation step, a histogram is computed for the region of each acquired image, the histogram representing the number of pixels for each intensity value; and the calculated indicator depends on the computed histogram;
  each histogram includes at least one peak, a darkest peak corresponding to the lowest intensity values; and the calculated indicator is a function of the most represented intensity value of the darkest peak;
  the estimated quantity of said analyte depends on the inverse of the most represented intensity value of the darkest peak;
  each histogram includes two peaks, a first peak being the darkest peak corresponding to the lowest intensity values, and a second peak corresponding to intensity values greater than the intensity values of the first peak; and the calculated indicator is a function of the number of pixels for the second peak;
  during the lighting step, the beam extends through the fluid chamber in a longitudinal direction; and during the acquisition step, the photodetector is positioned at a distance smaller than 1 cm from the fluid chamber in the longitudinal direction;
  the beam has a surface area comprised between 5 $mm^2$ and 200 $mm^2$ in a plane perpendicular to the longitudinal direction, said plane being arranged in contact with the fluid chamber; and the beam directly lights the fluid chamber, and the image is formed directly by the radiation transmitted by the lighted fluid chamber, in the absence of a magnifying lens positioned between the fluid chamber and the photodetector.

The invention also relates to an estimation system for estimating the quantity of an analyte contained in a liquid, the system comprising:

a fluid chamber configured for receiving the liquid and for mixing the liquid with a bi-specific reagent, the bi-specific reagent being configured for grafting on both a particle and an analyte present in the liquid;

a light source configured for emitting an excitation beam to light the fluid chamber, the beam extending through the fluid chamber;

a matrix photodetector configured for acquiring at least one image of a radiation transmitted by the lighted fluid chamber; and an information processing unit configured for estimating, from at least one acquired image, the quantity of said analyte in the liquid.

According to other advantageous aspects of the invention, the estimation system comprises one or more of the following features, considered alone or according to any technically possible combinations:

the liquid includes blood, and the bi-specific reagent is configured for grafting on both a blood particle and an analyte present in the liquid;

the blood particle is a red blood cell, the bi-specific reagent being configured for grafting on both the red blood cell and the analyte;

the analyte is a D-dimer;

the information processing unit is further configured for calculating an indicator for each acquired image, the indicator being representative of the intensity of the pixels of the image in a predetermined region of the image; and the quantity of said analyte is estimated according to said indicator;

the light source is configured for emitting the beam through the fluid chamber in a longitudinal direction; and the photodetector is positioned at a distance smaller than 1 cm from the fluid chamber in the longitudinal direction.

BRIEF DESCRIPTION OF THE DRAWINGS

These features and advantages of the invention will appear upon reading the following description, provided solely as a non-limiting example, and done in reference to the appended drawings, in which:

FIGS. 40 to 44 are images of the liquid characterized in FIGS. 30 to 34, respectively, obtained after dilution using a microscope and forming reference images.

DETAILED DESCRIPTION OF PREFERRED EMBODIMENTS

Figure 1:
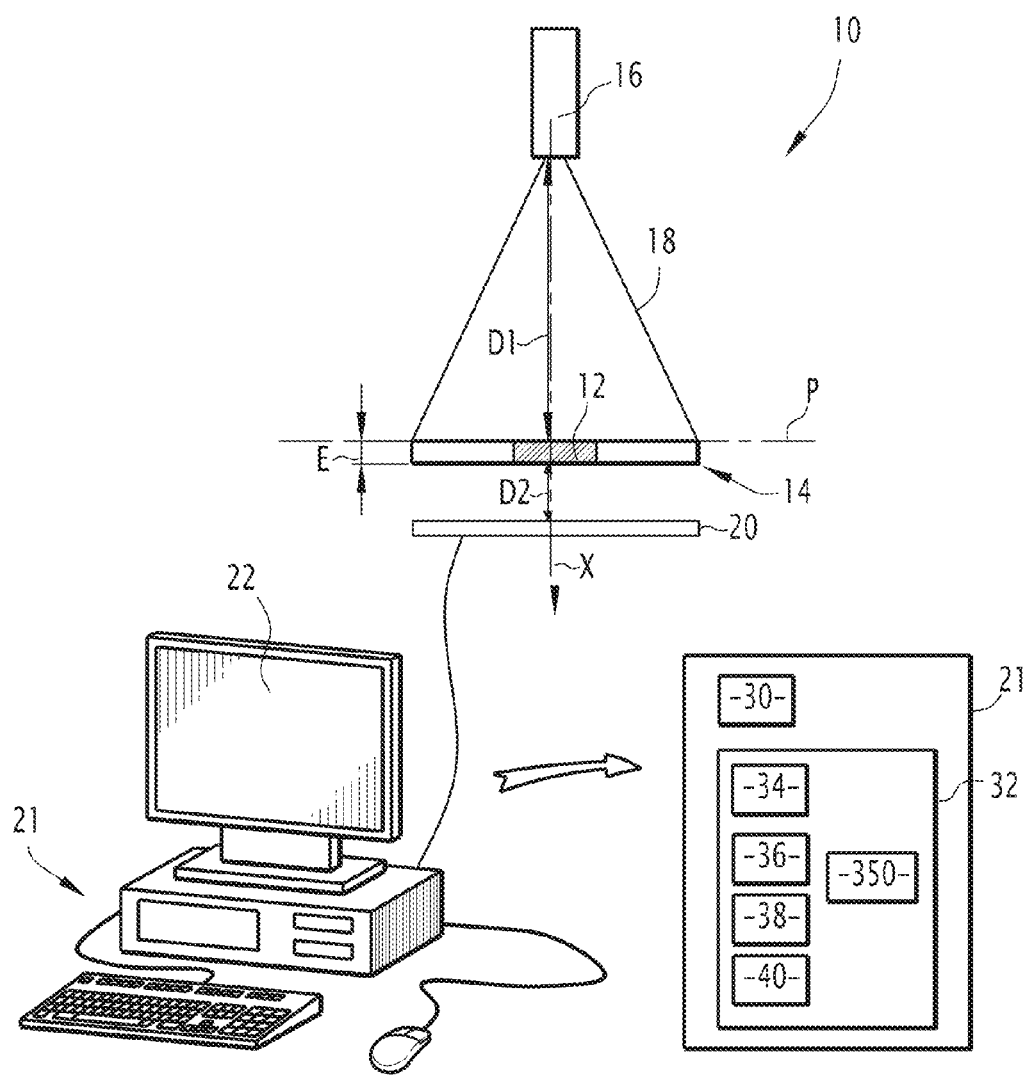
FIG. 1 is a very diagrammatic illustration of a characterization system according to the invention, comprising a fluid chamber receiving liquid to be characterized, a light source capable of lighting the chamber in a longitudinal direction, a matrix photodetector for acquiring images of the radiation transmitted by the lighted chamber and an information processing unit.

In FIG. 1, a characterization system 10 is designed to characterize a variation of the speed of particles or the agglomeration of particles, the particles, such as blood particles, being contained in a liquid 12, through the acquisition of images formed by a radiation transmitted by the lighted liquid 12, then processing those images. The variation of the speed of particles is, for example, a slowing of the particles as will be described in more detail hereafter. One skilled in the art will understand that the characterization system 10 according to the invention is similarly capable of characterizing the acceleration of the particles.

Thus, in general, the characterization system 10 is designed to characterize a parameter of a liquid comprising particles, that liquid in particular being blood. This parameter is, for example, a coagulation or an agglomeration of particles making up the liquid. Alternatively, it is a count of the particles or an observation of the morphology of the particles.

The term "particles" in particular refers to a biological particle, i.e., a cell (for example, a red blood cell, a white blood cell, or a platelet), a bacteria, a virus, or any other molecule (for example, a protein).

Agglutination (or agglomeration) refers to the formation of a three-dimensional structure of particles connected to each other, under the effect of a reagent that has been introduced.

Agglutination (or agglomeration) state refers to an estimate, which may be relative or absolute, of the size of the agglutinates or relative to the quantity of particles present in the agglutinates.

The characterization system 10 comprises a fluid chamber 14 designed to receive the liquid 12, a light source 16 capable of emitting an excitation laser beam 18 to light the fluid chamber 14, the laser beam 18 oriented in a longitudinal direction X through the fluid chamber 14, and a matrix photodetector 20 capable of acquiring images of the radiation transmitted by the fluid chamber 14 lighted by the laser beam 18. Transmitted radiation refers to the radiation passing through the fluid chamber, such that the matrix photodetector 20 and the light source 16 are situated on either side of the fluid chamber 14.

The characterization system 10 comprises an information processing unit 21 and a screen 22 for displaying an image of the chamber 14.

In the described embodiment, the characterization system 10 is capable of characterizing the coagulation of the blood or the agglutination of blood particles, the agglutination of blood particles making it possible to determine the associated blood group. The liquid 12 then contains blood. The liquid 12 is, for example, whole blood, a fraction of the blood, or a blood plasma. Alternatively, the liquid 12 is another bodily fluid, such as urine, perspiration, etc.

Figure 3:
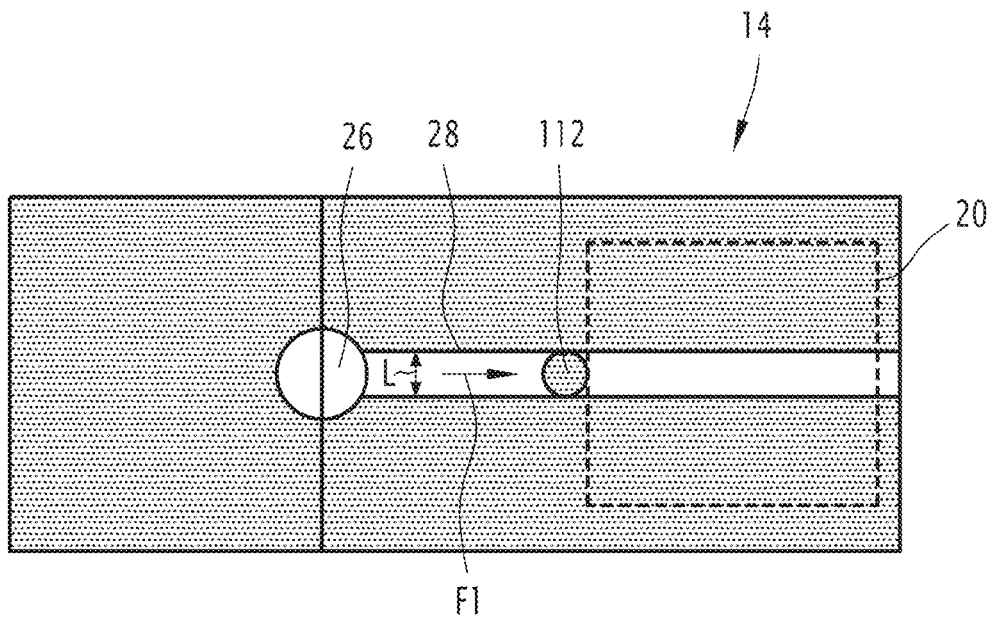
FIG. 3 is a diagrammatic view of the fluid chamber in the longitudinal direction, as well as the arrangement of the matrix photodetector of FIG. 1 relative to the chamber, according to a first alternative.

The fluid chamber 14 is positioned between the light source 16 and the matrix photodetector 20 in the longitudinal direction X. The fluid chamber 14 comprises a deposition area 26 of the liquid and one or more circulation channels 28 for the liquid 12, as shown in FIG. 3.

The fluid chamber 14 includes at least one fluid channel, delimited, in direction X, by an upper plate and a lower plate, not shown. These plates are at least partially translucent so as to make it possible to light the liquid 12 using the light source 16, as well as to detect the radiation transmitted by the matrix detector 20.

The lower and upper plates are, for example, glass slides, not shown, and separated by spacers, not shown, such that the glass slides are separated by approximately 160 µm in the longitudinal direction X.

The fluid chamber 14 has a thickness E in the longitudinal direction X. The thickness E for example has a value comprised between 20 µm and 1000 µm, preferably comprised between 30 µm and 300 µm.

The light source 16 is capable of emitting the laser beam 18 in the longitudinal direction X.

The light source 16 is positioned at a first distance D1 from the fluid chamber 14 in the longitudinal direction X. The first distance D1 preferably has a value comprised between 1 cm and 30 cm, for example equal to 20 cm.

In the described embodiment, the light source 16 is a spatially and temporally coherent source. The light source 16 is, for example, a laser. Alternatively, the light source 16 is a laser diode (LD) or a laser diode of the VCSEL (Vertical Cavity Surface Emitting Laser) type.

Also alternatively, the light source 16 is a light-emitting diode (LED), monochromatic and having small enough dimensions to be considered spatially coherent, the diameter of the LED being smaller than 1/10 of the first distance D1 separating that LED from the chamber.

The laser beam 18, oriented in the longitudinal direction X, has, at the level of the fluid chamber, a surface area comprised between 5 mm$^2$ and 200 mm$^2$, preferably equal to 25 mm$^2$, in a plane P perpendicular to the longitudinal direction X, as shown in FIG. 1. The plane P is arranged in contact with the fluid chamber 14. Thus, the lighted fluid surface is larger than in the state of the art. This makes it possible to eliminate local fluctuations of the parameter that one wishes to determine.

The laser beam 18 is capable of lighting the fluid chamber 14 directly, preferably in the absence of a magnification lens positioned between the light source 16 and the fluid chamber 14.

The matrix photodetector 20 is a pixelated image sensor, including a plurality of pixels, not shown. Each pixel of the photodetector 20 has dimensions smaller than or equal to 10 µm, or even 4 µm. Each pixel is, for example, square, each side having a value smaller than or equal to 10 µm, or even 4 µm. In the described embodiment, each pixel is in the form of a square with sides measuring 4 µm. Alternatively, each pixel is in the form of a square with each side measuring 2.2 µm.

The matrix photodetector 20 is positioned at a second distance D2 from the fluid chamber 14 in the longitudinal direction X. The second distance D2 has a value smaller than 1 cm, and preferably comprised between 100 µm and 2 mm. Favoring a short distance between the detector and the chamber makes it possible to limit the interference phenomena between the different diffraction patterns. In fact, when this distance increases, these interferences can make the image unusable, in particular when the number of diffracting particles increases. This is due to the fact that the volume of fluid that is lighted is greater than in the device described in application EP 2,233,923 A1 of the state of the art. By placing the detector at a distance of more than 1 cm away, the image obtained on the detector would be difficult to use.

The images acquired by the matrix photodetector 20 are formed by the radiation transmitted directly by the lighted fluid chamber 14, in the absence of a magnification lens positioned between the fluid chamber 14 and the matrix photodetector 20. The matrix photodetector 20 is also called a lensless imaging device, and is capable of forming an image of the fluid chamber 14 while being placed at a small distance therefrom. A small distance refers to a distance smaller than 1 cm.

The matrix photodetector 20 is capable of generating at least one image every 5 seconds, and the acquisition rhythm is therefore greater than 0.2 Hz. The matrix photodetector 20 is a two-dimensional image sensor, i.e., in a plane perpendicular to the longitudinal axis X. The acquisition frequency of the images is preferably comprised between 1 Hz and 20 Hz.

The matrix photodetector 20 is for example a CCD sensor. Alternatively, the photodetector 20 is a CMOS sensor.

The matrix photodetector 20 is for example substantially aligned with the fluid chamber 14 in the longitudinal direction X, as illustrated in FIG. 3, where the photodetector 20 is shown in dotted lines.

Figure 4:
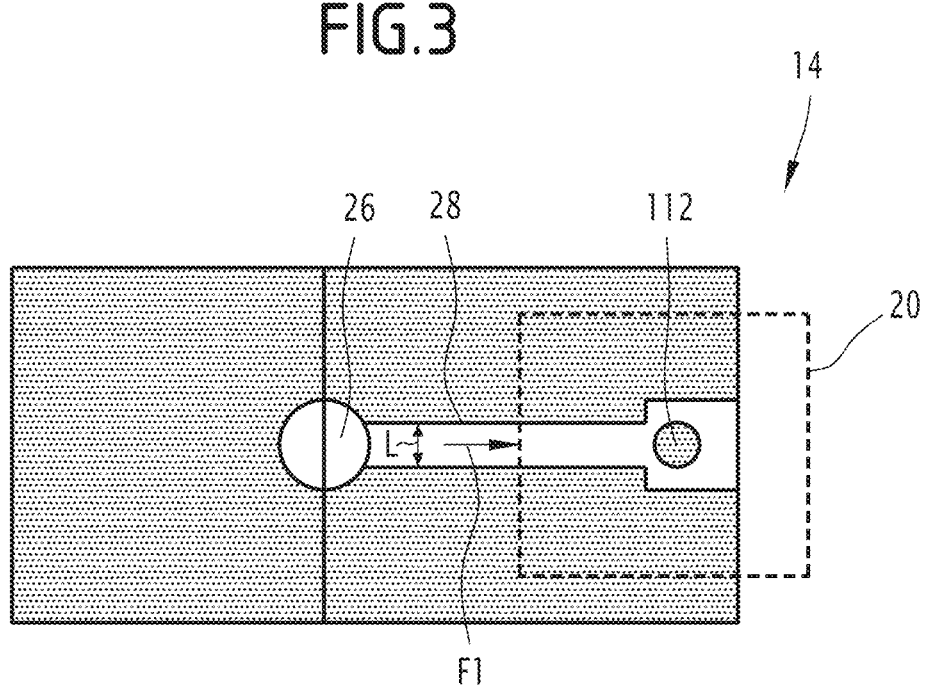
FIG. 4 is a view similar to that of FIG. 3 according to a second alternative.

Alternatively, the matrix photodetector 20 is slightly offset relative to the chamber 14 along the longitudinal axis X, as illustrated in FIG. 4, where the photodetector 20 is also shown in dotted lines.

The information processing unit 21, shown in FIG. 1, includes a data processor 30 and a memory 32 associated with the processor.

Figure 2:
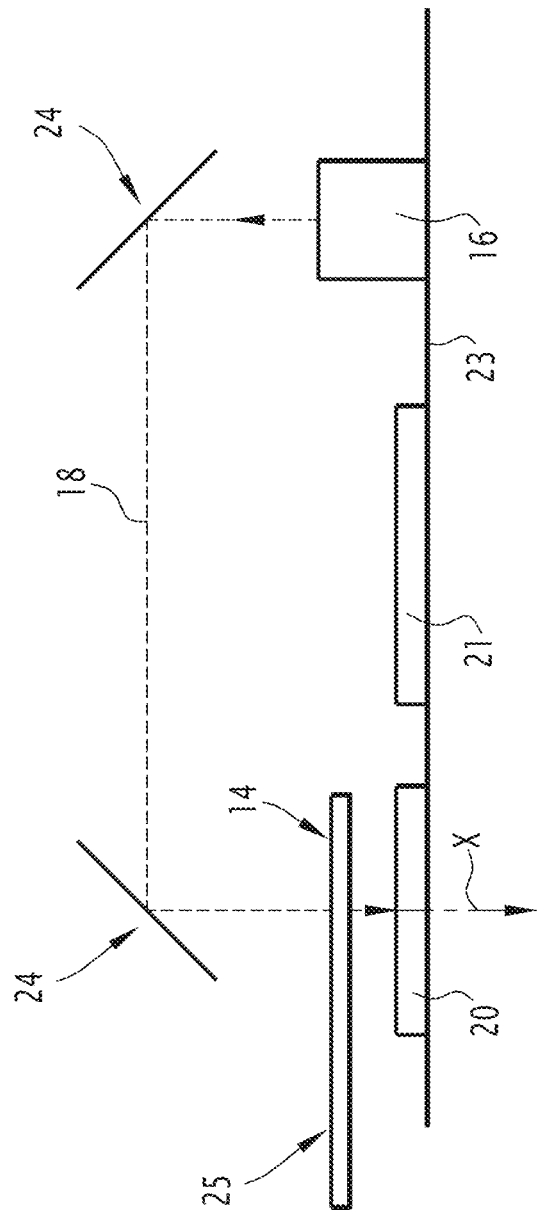
FIG. 2 is a very diagrammatic illustration of the characterization system according to the invention, according to another arrangement of the light source relative to the matrix photodetector.

In the example embodiment of FIG. 2, the matrix photodetector 20, the light source 16, and optionally all or part of the information processing unit 21 are secured to a second substrate 23. The characterization system 10 comprises an optical system 24, for example a mirror, making it possible to return the laser beam 18 from the light source 16 toward the photodetector 20. This makes it possible to have a compact system. The fluid chamber 14 is for example formed in a removable support 25. The removable support 25 is for example disposable and designed to be inserted overhanging the photodetector 20, at a small distance therefrom, such that the fluid chamber can be lighted by the laser beam 18. According to this example embodiment, the support 25 is designed to receive the fluid to be analyzed 12, then to be inserted near the photodetector 20 so that the analysis can be done. It for example includes a conduit, in which the fluid 12 circulates as far as the channel 28 of the fluid chamber, the fluid chamber 14 being connected to that conduit. When the analysis is complete, the support 25 is removed, in particular to be thrown away. The characterization system 10 is then available to perform another measurement with another support.

One skilled in the art will understand that, in the example embodiment of FIG. 2, the longitudinal direction X corresponds to the last portion of the laser beam 18 between the corresponding mirror of the optical system 24 and the photodetector 20, passing through the fluid chamber 14.

The or each circulation channel 28 has a width L, shown in FIGS. 3 and 4. The width L for example has a value comprised between 50 µm and 5 mm, preferably equal to 1.5 mm.

The memory 32 is capable of storing software 34 for receiving the images acquired by the matrix photodetector 20, first software 36 for calculating a first indicator $Ind1_{n,n+m}$ capable of characterizing the desired parameter; in this case, the variation of the speed of the particles, such as their slowing. Additionally or alternatively, the memory 32 can store second software 38 for calculating a second indicator $Ind2$ capable of characterizing another desired parameter, in this case the agglomeration of the particles. The memory 32 is also capable of storing software 40 for characterizing the variation of the speed of the particles and/or the agglomeration of the particles.

Alternatively, the reception means 34, the first calculation means 36, the second calculation means 38 and the characterization means 40 are made in the form of programmable logic components or in the form of dedicated integrated circuits.

The reception software 34 is capable of regularly receiving, from the photodetector 20, the images acquired sequentially at different moments. The reception software 34 is capable of receiving at least one image per second, and the reception rhythm of the images is greater than 0.2 Hz, typically from 1 Hz to 20 Hz.

The first calculation software 36 is capable of calculating an image $A_n$, representing the transmission image $I_n(x,y)$, from which a local mean is taken out. The latter is obtained by convoluting the image $I_n(x,y)$ with a kernel k1. This kernel k1 is a matrix with small dimensions relative to $I_n$. For example, the dimensions of the kernel k1 are 10 pixels by 10 pixels, and the dimensions of $I_n$ are at least twice as large as those of the kernel k1, or even 10 times larger. The kernel k1, including P rows and Q columns, is for example homogenous, all of its values being identical. According to the preceding, P and Q are integers, for example equal to 10. Thus, two images $A_n$ and $A$, are established, respectively corresponding to the moments n and n+m, m being an integer. In general, m is equal to 1, the transmission images $I_n$ and $I_{n+1}$ being two successive transmission images.

$$A_n(x,y) = I_n(x,y) - (I_n \otimes k1)(x,y) \tag{1}$$

$$A_{n+m}(x,y) = I_{n+m}(x,y) - (I_{n+m} \otimes k1)(x,y) \tag{2}$$

where $I_n(x, y)$, $I_{n+m}(x, y)$ represent two successive transmission images at moments n and n+m, x and y representing the coordinates of a point of the respective image, $I_n(x,y)$, $I_{n+m}(x,y)$ being matrices having X rows and Y columns, the symbol $\otimes$ representing the convolution integer defined by the following equation:

$$(F \otimes k1)(x, y) = \sum_{p=0}^{P} \sum_{q=0}^{Q} F(x-p, y-q) k1(p, q) \tag{3}$$

F being a matrix with X rows and Y columns, k1 representing a kernel for the correlation of the acquired images, k1 being a matrix with P rows and Q columns, X, Y, P and Q being Integers Verifying $X \geq P \geq 1$ and $Y \geq Q \geq 1$.

The images are for example acquired every second by the matrix photodetector 20, and the two transmission images $I_n(x,y)$, $I_{n+1}(x,y)$ are then images acquired with an interval of one second.

The first calculation software 36 is then capable of calculating a correlation image $Icorr_{n,n+m}(x,y)$ representative of the correlation between two transmission images $I_n(x,y)$, $I_{n+m}(x,y)$ for example according to the following equation:

$$Icorr_{n,n+m}(x, y) = \frac{((A_n \times A_{n+m}) \otimes k1)(x, y)}{\sqrt{((A_n^2) \otimes k1)(x, y)} \sqrt{((A_{n+m}^2) \otimes k1)(x, y)}} \tag{4}$$

where $Icorr_{n,n+m}(x,y)$ represents the correlation image of two transmission images $I_n$, $I_{n+m}$, established at respective moments n and n+m; x and y represent the coordinates of a point of the image, $Icorr_{n,n+m}(x,y)$ being a matrix with X rows and Y columns.

The first calculation software 36 is lastly capable of calculating the first indicator $Ind1_{n,n+m}$ from the correlation image $Icorr_{n,n+m}(x,y)$ previously obtained. This indicator $Ind1_{n,n+m}$ is representative of the intensity of the image $Icorr_{n,n+m}(x,y)$. This indicator $Ind1_{n,n+m}$ is then capable of characterizing the variation of the speed of the particles, such as their slowing.

The correlation indicator $Ind1_{n,n+m}$ is representative of the correlation between at least two transmission images $I_n(x,y)$ and $I_{n+m}(x,y)$ respectively acquired at moments n and n+m, that correlation being established for a region of interest 142 of the correlation image $Icorr_{n,n+m}(x,y)$. Said region of interest 142 is determined by the user. It corresponds to the area of the correlation image $Icorr_{n,n+m}(x,y)$ that one wishes to use to determine the correlation indicator $Ind1_{n,n+m}$. It is for example a square area having several dozen pixels per side, for example 50×50 pixels. The correlation indicator $Ind1_{n,n+m}$ translates the value of the intensity in that region of interest 142. It is in particular determined from the mean intensity or the total intensity in the region of interest 142 of the image $Icorr_{n,n+m}(x,y)$. That indicator $Ind1_{n,n+m}$ for example represents the mean intensity level or said total intensity in the region of interest 142.

Alternatively, the first calculation software 36 is capable of calculating intermediate images $C_n(x,y)$, $C_{n+m}(x,y)$ from two transmission images $I_n(x,y)$, $I_{n+m}(x,y)$ acquired at moments n and n+m, according to the following equation:

$$C_n(x,y) = I'_n(x,y) - \overline{I'_n} \quad (5)$$

$$C_{n+m}(x,y) = I'_{n+m}(x,y) - \overline{I'_{n+m}} \quad (6)$$

where $I'_n(x,y)$, $I'_{n+m}(x,y)$ respectively represent a region of interest of the two transmission images $I_n$ and $I_{n+m}$. As previously stated, the index m is for example equal to 1. The coordinates x and y designate the coordinates of a point of the image, $C_n(x,y)$, $C_{n+m}(x,y)$ being matrices having N rows and M columns, and $\overline{I'_n}$, $\overline{I'_m}$ representing a mean value of the respective regions of interest $I_n(x,y)$, $I_m(x,y)$. We must specify that the subtraction of $I'_n$ and $I'_m$ by $\overline{I'_n}$ and $\overline{I'_m}$, respectively, is optional. This corresponds to a normalization step, making it possible to obtain an indicator comprised between 0 and 1. Furthermore, this makes it possible to eliminate the fluctuation effect of the lighting intensity of the medium between two images.

According to this alternative, the first calculation software 36 is then capable of calculating the first indicator $Ind1_{n,n+m}$ according to the following equation:

$$Ind1_{n,n+m} = \frac{\sum_{x=1,y=1}^{N,M} \sqrt{C_n^2(x,y)} \sqrt{C_{n+m}^2(x,y)}}{\sqrt{\sum_{x=1,y=1}^{N,M} C_n^2(x,y)} \sqrt{\sum_{x=1,y=1}^{N,M} C_{n+m}^2(x,y)}} \quad (7)$$

where $Ind1_{n,n+m}$ represents the first indicator.

The characterization software 40 is capable of characterizing the variation of the speed and/or agglomeration of particles contained in the liquid 12. More specifically, the characterization software 40 is capable of determining, from the first calculated indicator $Ind1_{n,n+m}$, the variation of the speed of the particles contained in the liquid 12, such as their slowing. In the embodiment described where the liquid 12 contains blood, the first characterization software 40 is capable of determining, from the first calculated indicator $Ind1_{n,n+m}$, the coagulation of the blood particles and/or a time interval, called coagulation time, between an initial moment and the moment when the first calculated indicator $Ind1_{n,n+m}$ takes a predetermined value. Thus, in general, $Ind1_{n,n+m}$ characterizes a coagulation parameter of the blood, based on the observation of transmission images $I_n$, $I_{n+m}$ at moments n and n+m, m generally being comprised between 1 and 10, and preferably equal to 1.

Figure 5:
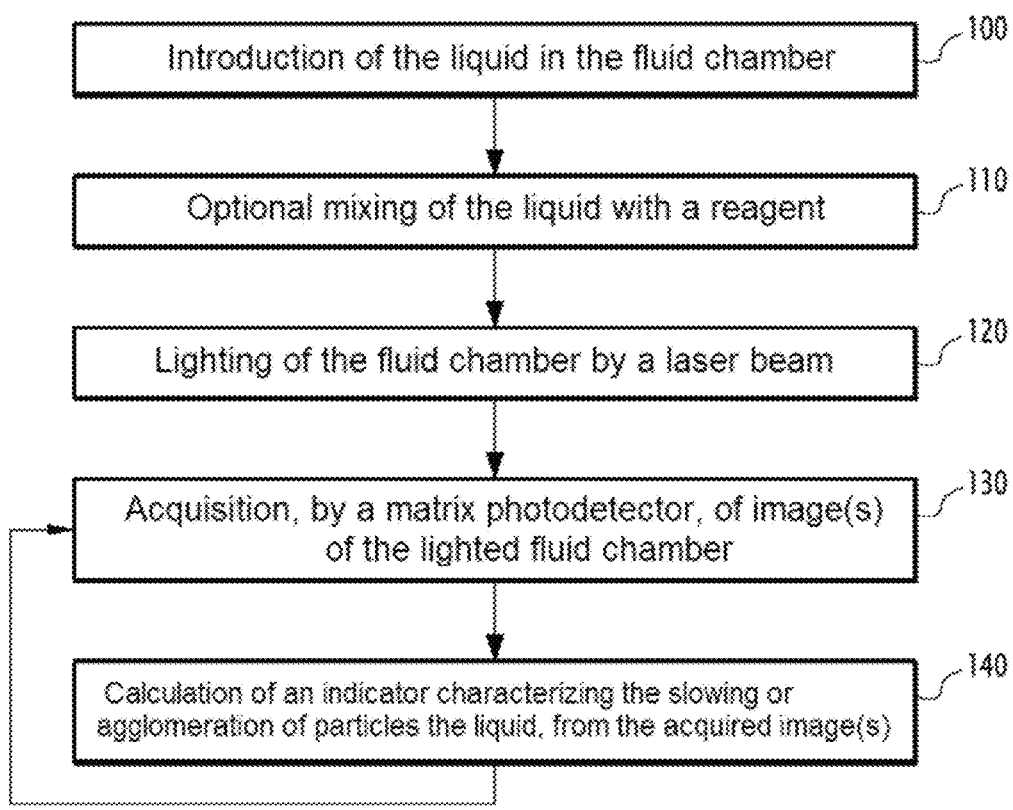
FIG. 5 is a flowchart of a characterization method according to the invention.

The operation of the characterization system 10 according to the invention will now be described using FIG. 5, showing a flowchart of the characterization method according to the invention.

Figure 6:
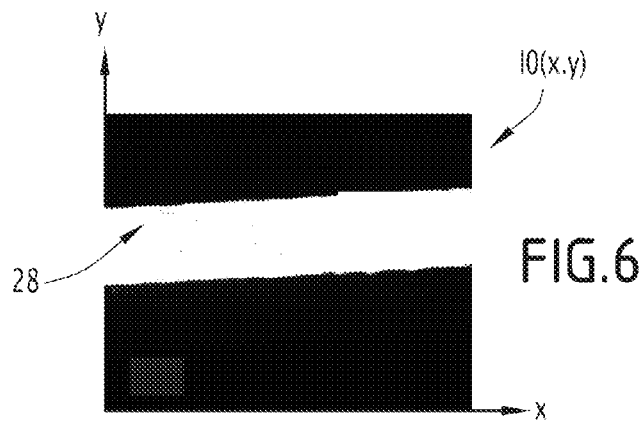
FIG. 6 is an image of an empty channel of the chamber of FIG. 1, acquired by the matrix photodetector.

Before use thereof, the circulation channel(s) 28 of the fluid chamber are empty, and an initial image $I_0$ of the chamber 14 then shows a white area corresponding to the circulation channel 28 and areas delimiting the channel, in this example appearing in the form of dark areas corresponding to the rest of the fluid chamber 14, as shown in FIG. 6.

During the initial step 100, the liquid 12 is introduced into the deposition area 26 of the fluid chamber. The liquid 12 flows by capillarity in the deposition area 26 toward the circulation channel(s) 28.

The liquid 12 is then optionally, in step 110, mixed with a reagent 112, shown in FIGS. 3 and 4, and capable of triggering or favoring a slowing phenomenon of the particles. The reagent 112 is, for example, a lyophilized reagent capable of favoring the slowing of the blood particles through coagulation of the blood.

The reagent 112 is, for example, deposited upstream from the optical detection area corresponding to the area inside the dotted lines in FIG. 3 for which an image is acquired by the photodetector 20. Alternatively, the reagent 112 is positioned inside the optical detection area, as shown in FIG. 4. The mixing between the liquid 12 and the reagent 112 occurs when the liquid 12 flows in contact with the reagent 112 inside the circulation channel 28 (arrow F1).

In the described embodiment, the reagent 112 is a procoagulant protein. This protein is deposited, dried or lyophilized in the circulation channel 28. The reagent 112 is for example the prothrombin protein, also called PT, when the INR (International Normalized Ratio) parameter is being determined.

$$INR = \left(\frac{T}{Tref}\right)^{ISI} \quad (8)$$

T being the measured coagulation time, Tref being the considered reference time, ISI being a correction factor that depends on the reagents used to trigger the coagulation.

Alternatively, the reagent 112 is the Ecarin protein, when the coagulation time is measured using the ECT (Ecarin Clotting Time) test. Alternatively, the reagent 112 is the Thrombin protein when the coagulation time is measured using the TT (Thrombin Time) test.

The liquid 12 is lighted by the laser beam 18 during the step 120. The light source 16 in fact emits the laser beam 18 toward the fluid chamber 14 in which the liquid 12 is found in the longitudinal direction X.

During the step 130, the matrix photodetector 20 then sequentially acquires several transmission images $I_n(x,y)$, $I_{n+m}(x,y)$ at different moments n and n+m. Each transmission image $I_n(x,y)$, $I_{n+m}(x,y)$ is formed by the transmitted radiation, and the corresponding acquisition moment, by the lighted fluid chamber 14.

Figures 7, 8:
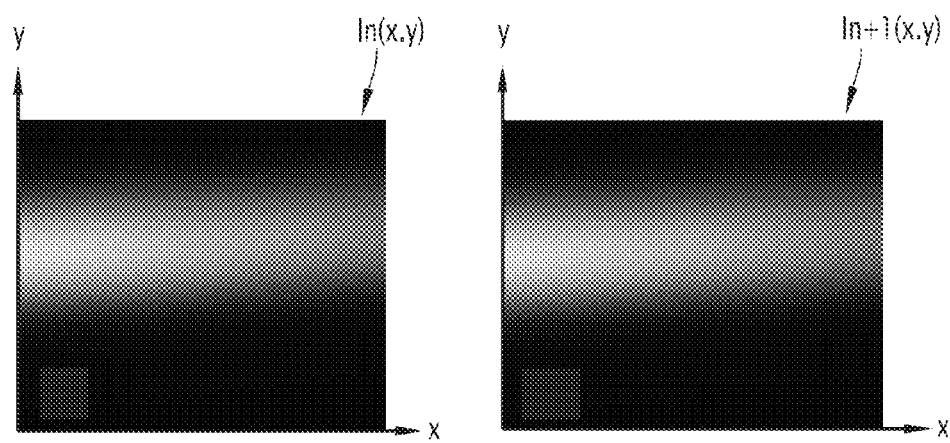
FIGS. 7 and 8 are images of the chamber containing the liquid, acquired by the photodetector at different moments.

The images $I_n(x,y)$, $I_{n+m}(x,y)$ are for example immediately successive images, m then being equal to 1, preferably acquired every second, as shown in FIGS. 7 and 8, where the time gap between the two images $I_n(x,y)$, $I_{n+1}(x,y)$ successively acquired is equal to 1 second.

The acquired images $I_n(x,y)$, $I_{n+1}(x,y)$ correspond to the interferences of diffraction patterns created by particles suspended in the liquid 12. The lighting of the particles by the spatially and temporally coherent beam 18, such as a laser beam, creates a diffraction pattern, which varies over time due to the movement of particles contained in the liquid 12.

The observation of a usable diffraction pattern, by placing the matrix photodetector 20 at such a small distance away, is in particular due to the absence of a magnification lens between the fluid chamber 14 and the photodetector 20.

During the acquisition step 130, the photodetector 20 is positioned at a small distance from the fluid chamber 14, the second distance D2 between the fluid chamber 14 and the photodetector 20 in the longitudinal direction X being smaller than 1 cm. At the end of the acquisition step 130, in particular after the acquisition of the images $I_n(x,y)$, $I_{n+1}(x,y)$, the first calculation software 36 begins, in the step 140, by calculating the images $A_n(x,y)$, $A_{n+1}(x,y)$ using equations (1), (2) and (3).

The first calculation software 36 then calculates the corresponding correlation image $Icorr_{n,n+1}(x,y)$ from the images $A_n(x,y)$, $A_{n+1}(x,y)$ and using equation (4).

Figures 9, 10:
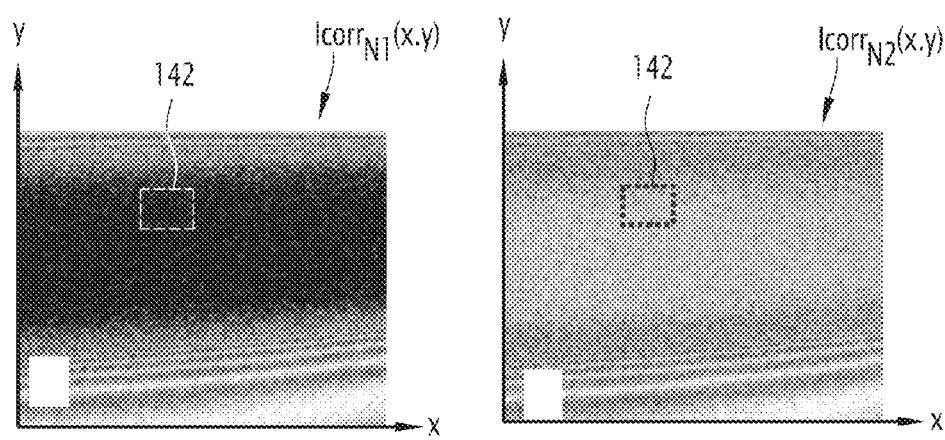
FIGS. 9 and 10 are correlation images, calculated by the processing unit of FIG. 1, from images acquired at different moments.

In the described embodiment, the correlation images evolve as a function of time, as shown in FIGS. 9 and 10, where the correlation image $Icorr_{N1,N1+1}(x,y)$, denoted $Icorr_{N1}(x,y)$, corresponding to correlation between two transmission images $I_n$, $I_{n+1}$ done with n=N1 before the coagulation (FIG. 9), has a very different appearance from the image $Icorr_{N2}(x,y)$ corresponding to a correlation between two transmission images $I_{N2}$, $I_{N2+1}$, done with n=N2 after the coagulation (FIG. 10).

The first calculation software 36 lastly calculates the value of the first indicator $Ind1_{n,n+1}$ for each correlation image $Icorr_{n,n+1}(x,y)$ obtained. The value of the first indicator $Ind1_{n,n+1}$ is for example the mean value of the points of the correlation image $Icorr_{n,n+1}(x,y)$ in the predetermined region of interest 142, visible in FIGS. 9 and 10. Alternatively, the value of the first indicator $Ind1_{n,n+1}$ is the integral of the image in the region of interest 142 (i.e., the sum of the gray levels of each pixel). Also alternatively, the value of the first indicator $Ind1_{n,n+1}$ is a function of that integral.

Alternatively, the first calculation software 36 begins, in step 140, by calculating the intermediate images $C_n(x,y)$, $C_{n+1}(x,y)$ using equations (5) and (6).

The first calculation software 36 then populates the value of the first indicator $Ind1_{n,n+1}$ from intermediate images $C_n(x,y)$, $C_{n+1}(x,y)$ and using equation (7).

In the described embodiment, at the end of the calculation step 140, the characterization method returns to step 130 in order to acquire a new image of the lighted fluid chamber 14, then to calculate, similarly to during step 140, a new correlation image $Icorr_{n+1,n+2}(x,y)$ and a new value of the first indicator $Ind1_{n+1,n+2}$.

The acquisition 130 and calculation 140 steps are then reiterated regularly, for example every second, for a predetermined length of time, for example longer than 60 seconds, or until a stop initiated by the user, in particular in light of the evolution over time of the first indicator.

Figure 11:
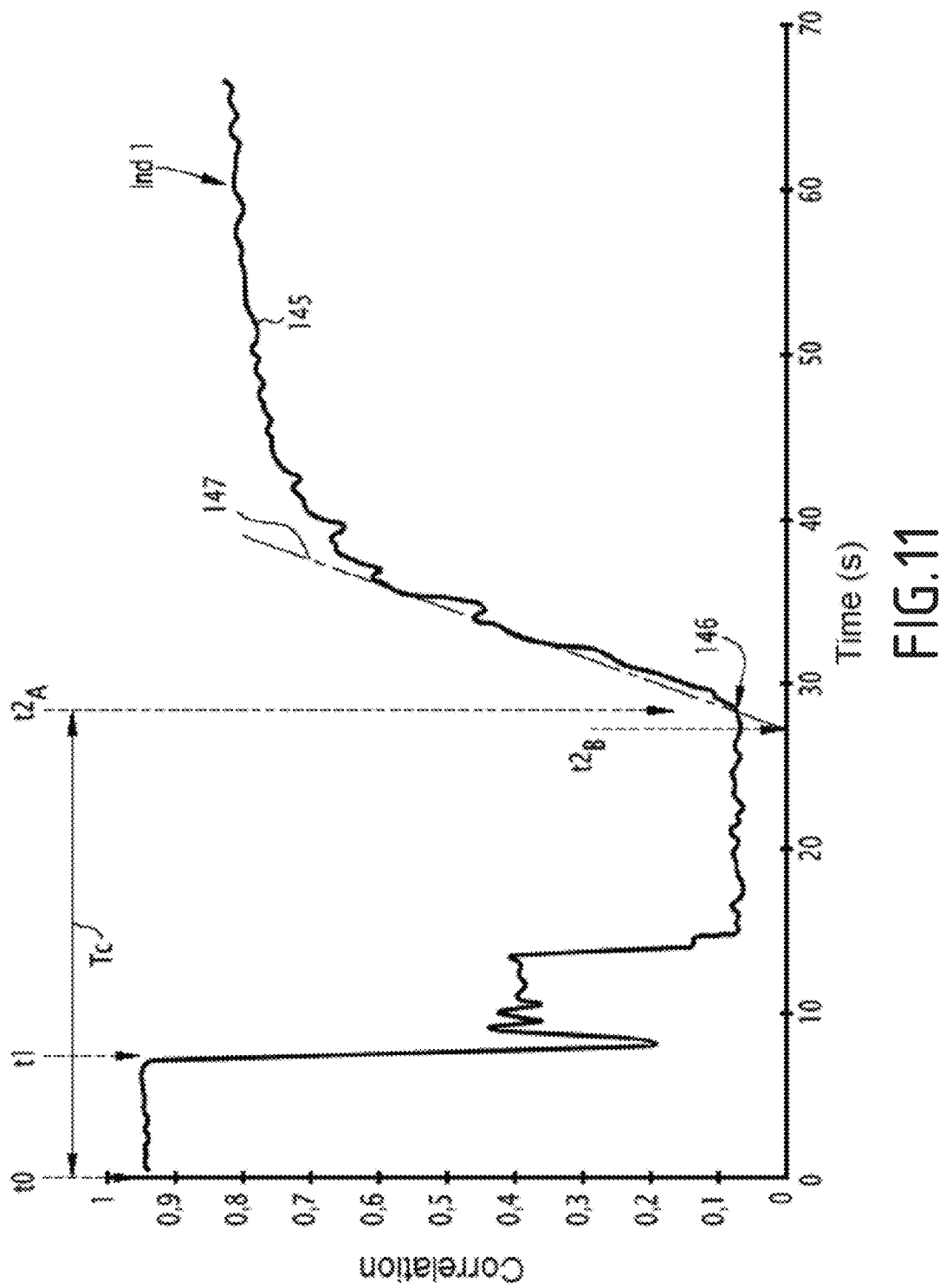
FIG. 11 is a depiction of the evolution over time of an indicator characterizing a variation of the speed of the particles contained in the liquid, such as a slowing of the particles.
Figure 12:
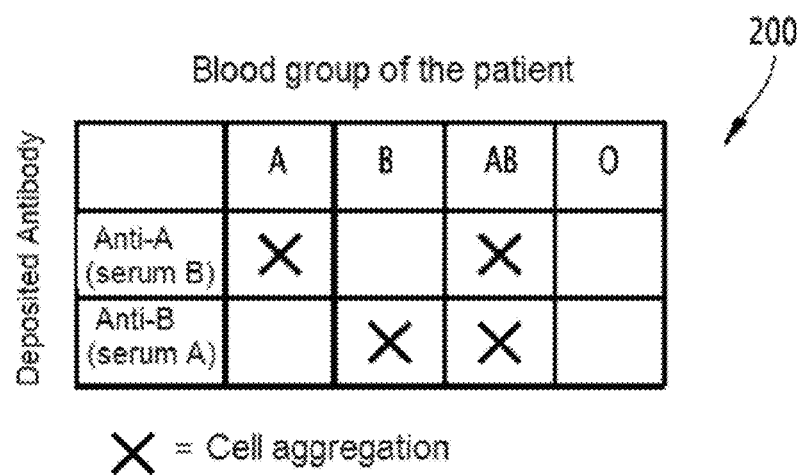
FIG. 12 is a table illustrating the case of cell aggregations as a function of the blood group and the antibody deposited.

The evolution over time of the first indicator $Ind1_{n,n+m}$, shown in the embodiment described by the curve 145 shown in FIG. 11, then makes it possible to calculate the variation of the speed of the particles contained in the liquid 12, such as the slowing of the blood particles.

In FIG. 11, an initial moment t0 corresponds to the mixture of the reagent 112 with the liquid 12, and the circulation channel 28 across from the optical detection area is then filled at a first moment t1. In other words, the example embodiment of FIG. 11 corresponds to the case where the reagent 112 is deposited just before the optical detection area, as shown in FIG. 3.

The curve 145 then shows, from the first moment t1, a decrease in the value of the first indicator $Ind1_{n,n+m}$ to reach a minimum value of less than 0.1. The curve 145 then shows, from the second moment $t2_A$, a rapid increase in the value of the first indicator $Ind1_{n,n+m}$ until that value stabilizes around 0.8.

The phase between the first and second moments t1, $t2_A$, also called first phase, during which the value of the first indicator $Ind1_{n,n+m}$ is low, corresponds to a low correlation between the transmission images successively acquired. In fact, this is due to a significant change in the diffraction pattern from one image to the other during the first phase, due to the movement of the particles suspended in a liquid 12, in the space corresponding to the region of interest 142.

The phase beginning at the second moment $t2_A$ and until the end of the characterization, also called second phase, corresponds to a swelling of the particles in a liquid 12, which amounts to an increase in the correlation between the successive images.

The characterization software 40 then determines, from the first populated indicator $Ind1_{n,n+m}$, the time interval between the initial moment t0 and the moment $t2_A$ at which the first indicator again has increasing correlation values. The time interval between the original moment t0 and the second moment $t2_A$ is also called coagulation time Tc. In the example embodiment of FIG. 11, the coagulation time Tc is approximately equal to 29 s.

The characterization software 40 also determines the coagulation of blood particles from the first populated indicator $Ind1_{n,n+m}$. The coagulation time T for example corresponds to the time gap between the initial moment t0 (t=0 on curve 145 in FIG. 11) and the coagulation moment, which characterizes the coagulation of blood.

This coagulation moment for example corresponds to a point where the curve 145 reaches a plateau, beyond which the values of the first indicator $Ind1_{n,n+m}$ practically no longer evolve (second moment $t2_A$). It will then be understood that this coagulation moment $t2_A$ can also be determined from the derivative of the time function describing the evolution of the first indicator $Ind1_{n,n+m}$, for example when the latter drops below a certain threshold.

Alternatively, this regulation moment is determined from the second derivative of that function. From that second derivative, it is possible to situate an inflection point 146 of the curve 145. The moment $t2_A$ corresponding to that inflection point 146 is then for example used to determine the coagulation moment.

In the example embodiment of FIG. 11, a tangent 147 to the curve 145 is drawn, passing through said inflection point 146. The coagulation moment then corresponds to the abscissa at which said tangent 147 crosses the baseline of said curve (second moment $t2_A$) or the abscissa at which said tangent 147 crosses the x-axis (third moment $t2_B$). A baseline refers to the portion of the curve, substantially planar, preceding the sharp increase in the value of the first indicator $Ind1_{n,n+m}$. In the illustrated example, the baseline corresponds to the portion of the curve 145 whereof the abscissa are comprised between approximately 15 seconds and 28 seconds (second moment $t2_A$).

As previously indicated, the coagulation time T is obtained by a difference between the coagulation moment $t2_A$, $t2_B$ and the initial moment t0, chosen at the origin of the x-axis of the curve 145.

The characterization system 10 and the characterization method according to the invention therefore make it possible to characterize the variation of the speed of the particles contained in the liquid 12 over a large portion of the circulation channel(s) 28 of the fluid chamber due to the small distance between the fluid chamber 14 and the photodetector 20.

In the example embodiment of FIG. 11, the characterization system 10 and the characterization method according to the invention make it possible to characterize a slowing of the particles by detecting an increase in the correlation between the successive images.

One skilled in the art will understand that the characterization system 10 and the characterization method according to the invention make it possible, similarly, to characterize an acceleration of the particles by detecting a decrease in the correlation between the successive images.

The second distance D2 smaller than 1 cm between the fluid chamber 14 and the photodetector 20 also makes it possible to limit the bulk of the characterization system 10.

Further, the significant scope of the laser beam 18 along the plane P, i.e., greater than 5 mm², and for example comprised between 5 mm² and 200 mm², makes it possible to limit the heating of the liquid 12 contained in the fluid chamber 14. In fact, the significant surface area of the laser beam 18 makes it possible to have an optical density with a low power.

Furthermore, using an extended laser beam and forming an image of the small distance from the chamber makes it possible to examine an even larger volume of fluid. The influence of local phenomena capable of becoming predominant when the laser beam is finer is then eliminated, and the volume of analyzed fluid is practically unique. Analyzing the correlation between two transmission images $I_n$, $I_{n+m}$ makes it possible to take into account the spatial structure of the coagulation, in the plane of the microfluidic channel 28. In other words, the evolution of the coagulation of the blood is observed in two dimensions.

FIGS. 12 to 17 illustrate a second embodiment for which the elements similar to the first embodiment previously described are identified using identical references, and are not described again.

According to the second embodiment, the characterization system 10 is designed more particularly to characterize the agglomeration of particles contained in a liquid 12. The characterization system 10 is for example capable of characterizing the agglomeration of blood particles, such as red blood cells, also called agglutination of blood particles.

Information relative to the blood group is then also determined from the agglomeration state, also called agglutination state.

As known per se, the blood group can be determined using the Beth-Vincent test by detecting the presence of A or B antigens implying the absence of anti-A or anti-B antibodies. In the case where the erythrocytes of the tested blood have an A or B antigen, an antigen-antibody complex will be formed and lead to a cellular aggregation as recalled in table 200, shown in FIG. 12.

Figure 13:
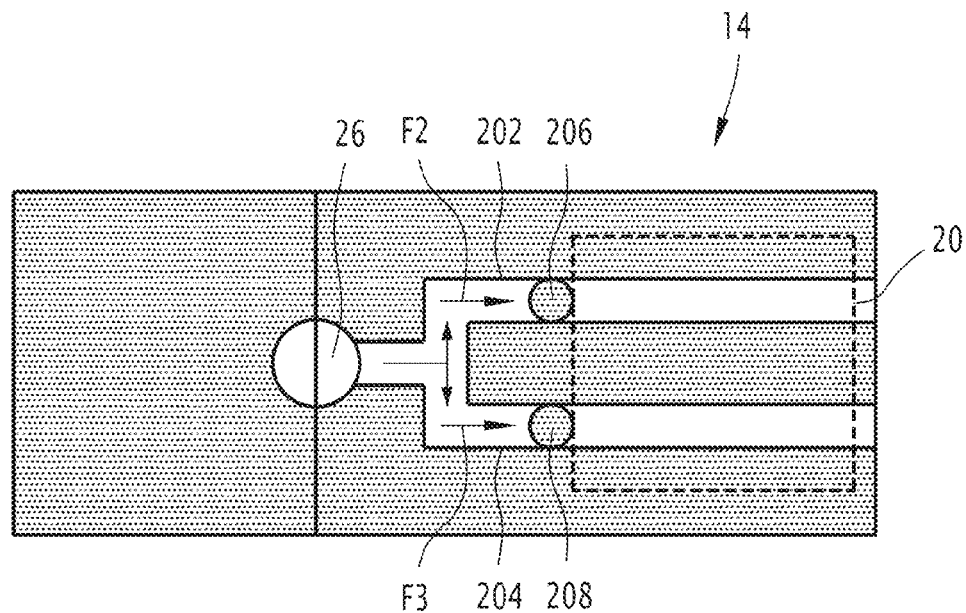
FIG. 13 is a view similar to that of FIGS. 3 and 4 according to a second embodiment, the fluid chamber including two channels.

The fluid chamber 14 includes two separate circulation channels 202, 204, i.e., a first channel 202 and a second channel 204, as shown in FIG. 13.

According to the second embodiment, the light source 16 is any type of light source. The laser 16 is not necessarily spatially and temporally coherent.

According to the second embodiment, the second calculation software 38 is able to calculate the second indicator Ind2 capable of characterizing the agglomeration of the particles, the second indicator Ind2 being an intensity indicator for each acquired image $I_n(x,y)$. The second indicator Ind2 is representative of the histogram of the intensity of each pixel in the image $I_n$, or in a region of interest thereof. It is determined for example by measuring the total intensity of the image $I_n$ or in a predetermined region of interest of the image $I_n$, optionally after thresholding.

The characterization software 40 is next capable of determining an agglomeration state of the particles of the liquid 12 from the second calculated indicator Ind2. The agglomeration state is for example determined when the second indicator Ind2 exceeds a predetermined threshold.

In the described embodiment, where the liquid 12 contains blood, the particles are for example red blood cells, and the characterization software is then capable of determining information relative to the blood group from the agglomeration state.

The operation of the second embodiment will now be described using FIGS. 13 to 17.

During the initial step 100, the liquid 12, for example the blood sample of a donor whereof one wishes to determine the blood group, is introduced into the deposition area 26 of the fluid chamber. The liquid 12 then flows from the deposition area 26 toward the circulation channels 202, 204, for example by capillarity.

The liquid 12 is then mixed with first 206 and second 208 distinct reagents, during step 110, as shown in FIG. 13.

Each reagent 206, 208 is for example deposited upstream from the optical detection area corresponding to the area inside the dotted lines in FIG. 13 for which an image is acquired by the photodetector 20.

The mixture between the liquid 12 and the first and second reagents 206, 208 is done when the liquid 12 flows into contact with the first reagent 206 inside the first channel 202 (arrow F2), and respectively the second reagent 208 inside the second channel 204 (arrow F3).

In the described embodiment, the first reagent 206 is a donor A serum, i.e., containing anti-B antibodies, and the second reagent 208 is a donor B serum, i.e., containing anti-A antibodies.

Depending on the blood group associated with the blood sample 12, a cellular aggregation will or will not then occur in each of the circulation channels 202, 204.

The liquid 12, such as the blood sample mixed with the first and second reagents 206, 208, is then lighted by the light beam 18 during step 120.

During step 130, the matrix photodetector 20 then acquires a transmission image I(x,y) corresponding to an optical detection area encompassing the two circulation channels 202, 204.

One skilled in the art will observe that, according to the second embodiment, the acquisition of a single transmission image I(x,y) makes it possible to characterize the agglomeration of the particles contained in the liquid 12, by comparing that image with a reference image $I_{ref}(x,y)$, the latter for example being an image made over a reference area, not shown, in which the blood is not mixed with the reagent. This reference area is for example a third channel, with a geometry identical to that of the first or second channel 202, 204, and not including any reagent.

Alternatively, this is an area situated on the first channel 202 or on the second channel 204, upstream from the reagent 206, 208.

Alternatively, the reference image $I_{ref}(x,y)$ is produced at the same location as the transmission image, just after filling of the channel by the analyzed liquid, the transmission image $I(x,y)$ being done, under the same conditions, after certain time, for example 1 minute, such that any effect of the reagent on the analyzed liquid is measurable.

The acquired image $I(x,y)$ corresponds similarly to the diffraction and the diffusion of the light beam 18 by the particles suspended in a liquid 12. Preferably, this image is done under identical conditions for the two channels, as well as for the reference area. For identical conditions, we particularly refer to the lighting conditions, the source-detector distance, the characteristics of the detector used, the placement time, the observed field, the size of the image.

The lighting of the particles by the laser beam 18 creates a diffraction pattern. As previously indicated, the absence of a magnification lens between the fluid and the photodetector 20, coupled with the significant surface of the incident beam, makes it possible to form a usable image at a short distance, covering a large fluid field, such as a field having an area of several millimeters squared.

During the acquisition step 130, the photodetector 20 is placed near the fluid chamber 14, the second distance D2 between the fluid chamber 14 and the photodetector 20 in the longitudinal direction X being smaller than 1 cm.

Figure 14:
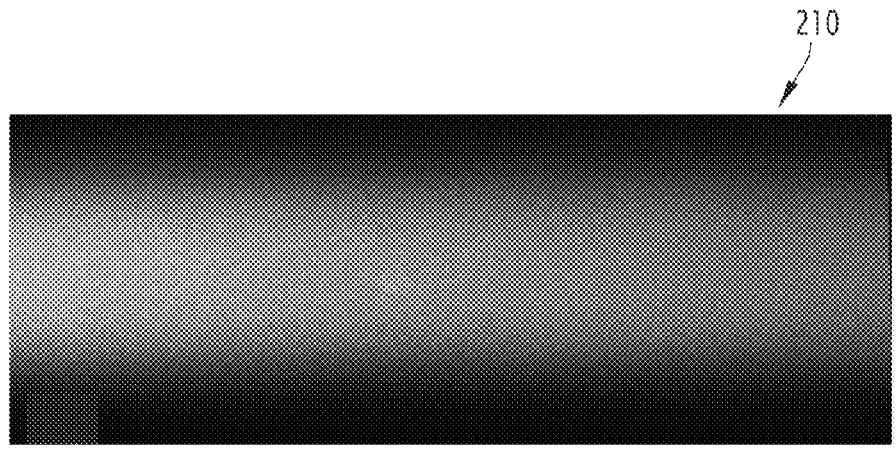
FIGS. 14 and 15 are respective images of the first and second channels of the chamber of FIG. 13, the second channel having a cell aggregation, the images being acquired by the photodetector of FIG. 1, FIGS. 16 and 17 are histograms of the gray level of the images acquired in FIGS. 14 and 15, FIGS. 18 to 21 are images of the liquid to be characterized, acquired by the photodetector according to a second example of the second embodiment, the liquid to be characterized containing blood, to which a variable quantity of antibodies is added, these images being acquired for increasing quantities of antibodies.
Figure 15:
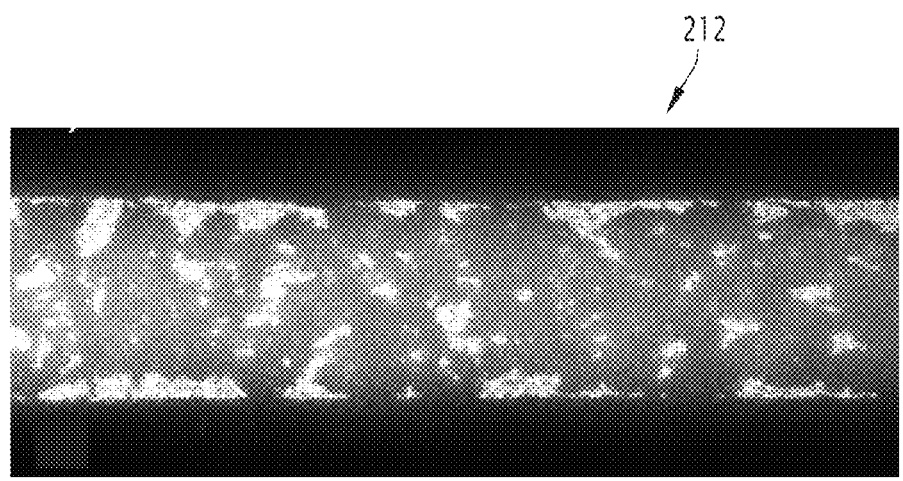

In the example embodiment of FIG. 14, showing an acquired image 210 of the first channel 202, and respectively an acquired image 212 of the second channel 204, the cellular aggregation is observed only in the second channel 204 through the presence of white stains in the image 212. In other words, the blood group associated with the tested blood sample is group B according to the table 200 of FIG. 12.

At the end of the acquisition step 130, the second calculation software 38 calculates, during step 140, the second indicator Ind2 able to characterize the agglomeration of the particles, the second indicator Ind2 being an intensity indicator for each acquired image $I(x,y)$. The second indicator Ind2 is representative of the intensity in the predetermined region of interest of the image, in particular the distribution of the intensity of the pixels in said region.

Figure 16:
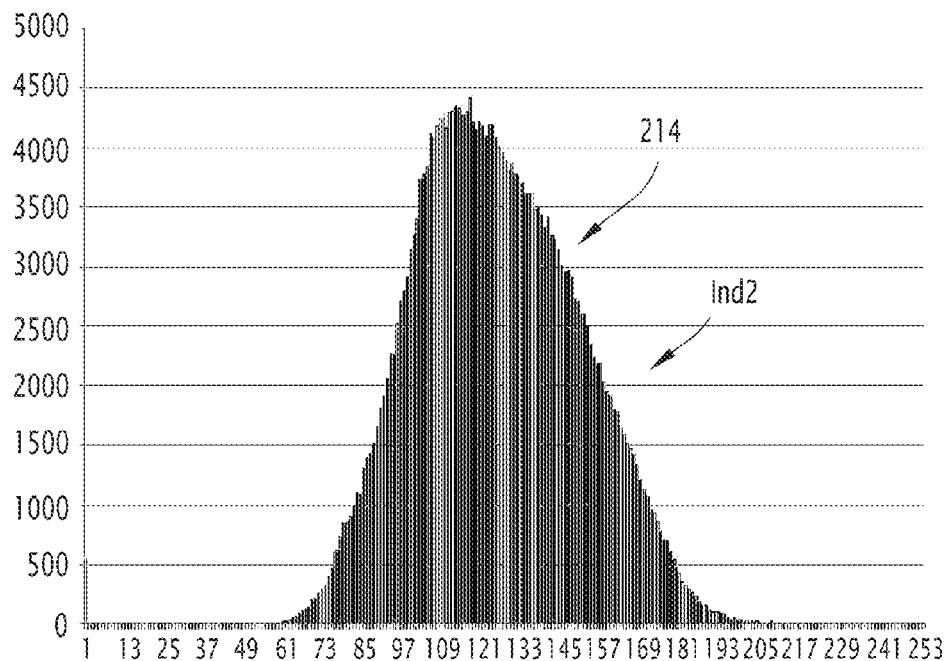
Figure 17:
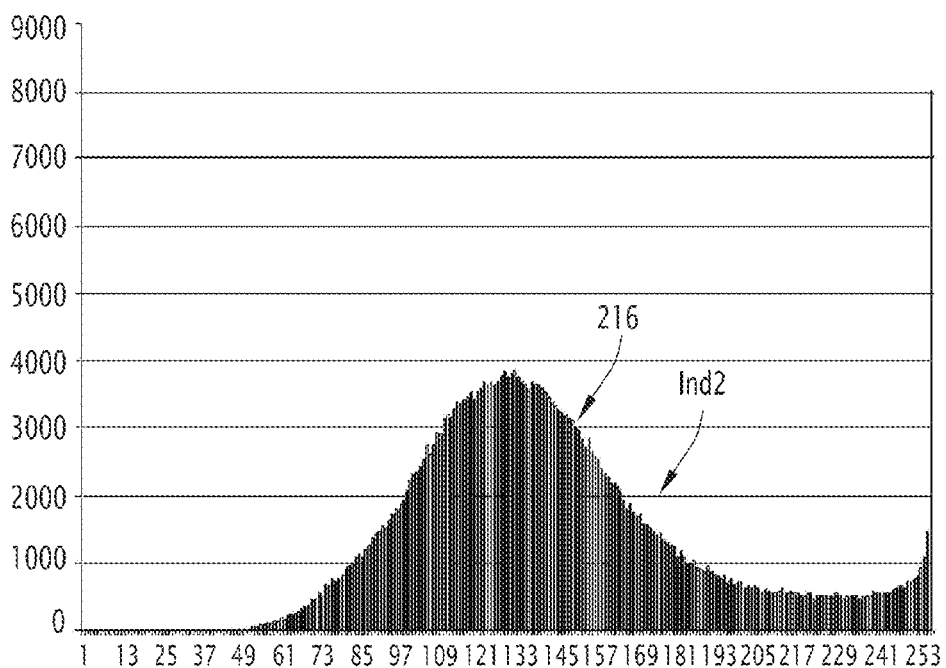
Figure 18:
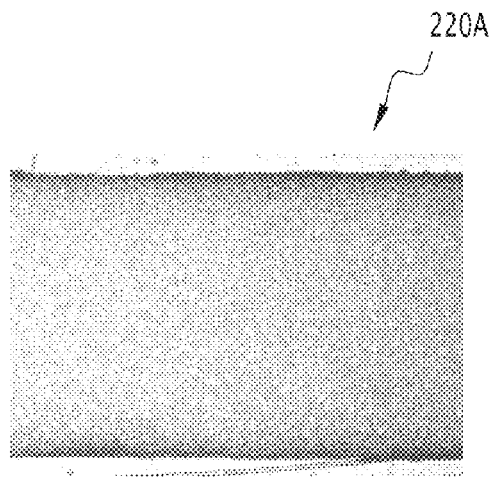
Figure 19:
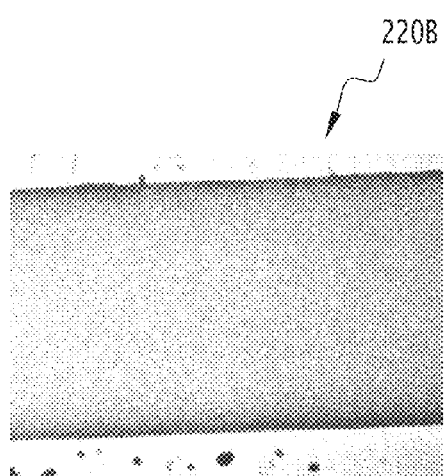
Figure 20:
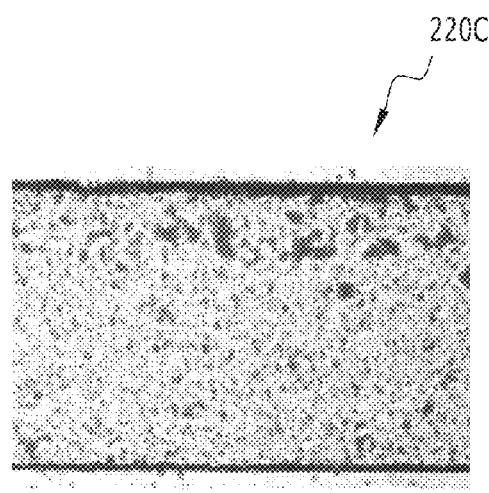
Figure 21:
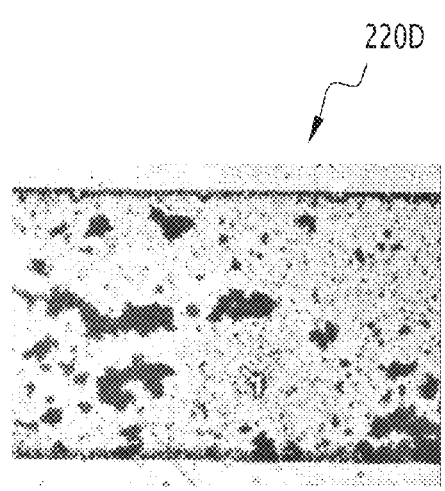
Figure 22:
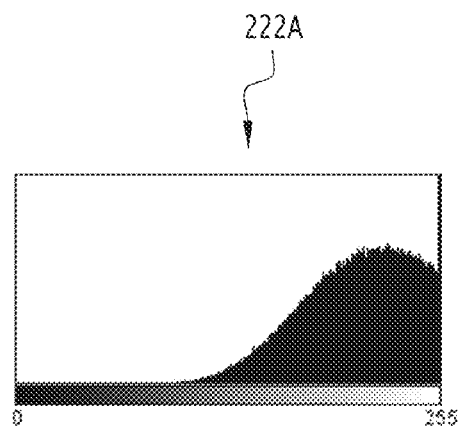
FIGS. 22 to 25 are histograms of the gray level of the images acquired in FIGS. 18 to 21, respectively.
Figure 23:
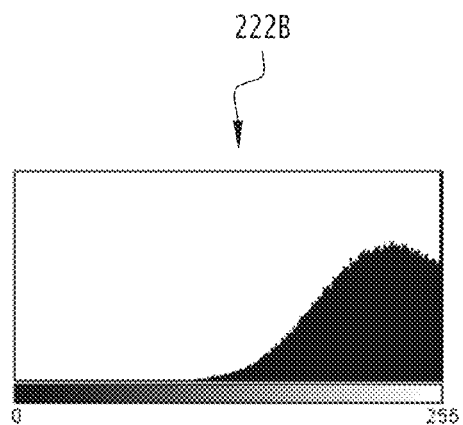
Figure 24:
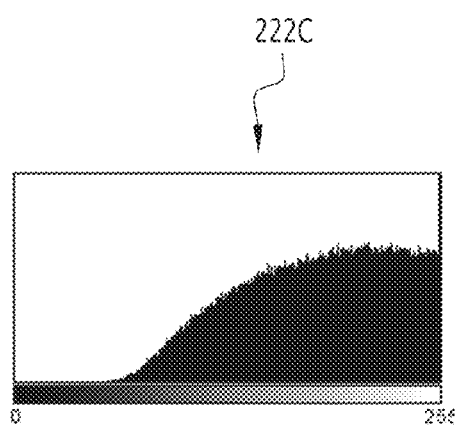
Figure 25:
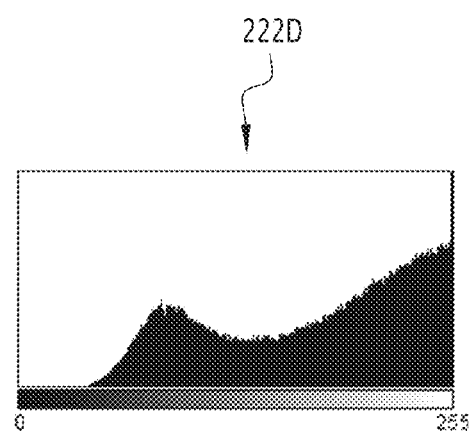
Figure 26:
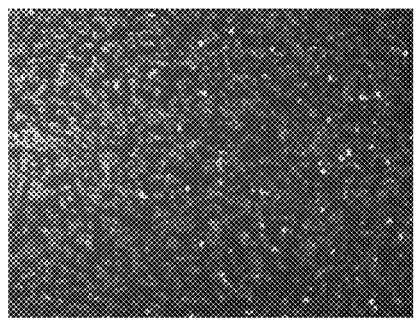
FIGS. 26 to 29 are images of the liquid characterized in FIGS. 18 to 21, respectively, obtained, after dilution, using a microscope and forming reference images.
Figure 27:
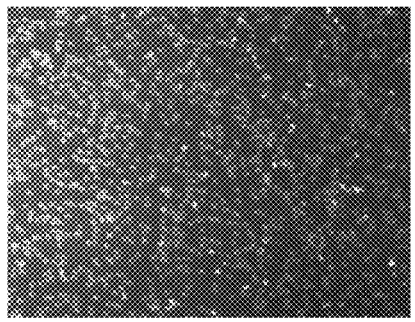
Figure 28:
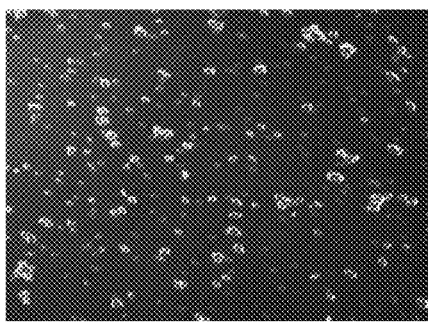
Figure 29:
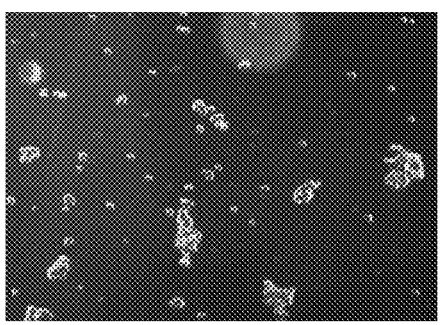

The second indicator Ind2 is, for example, a characteristic of the image, and in particular of histogram of the gray level of the image acquired for each channel 202, 204, and, if applicable, the reference channel as illustrated in FIGS. 16 and 17, showing a histogram 214 of the gray level of the acquired image of the first channel 202, and respectively a histogram 216 of the gray level of the acquired image of the second channel 204. Each gray level histogram 214, 216 has the gray level values on the x-axis and the pixel population on the y-axis, i.e., the number of pixels, for a gray level given on the x-axis. A characteristic of the histogram is for example the mean intensity of the pixels, denoted $I_{mean}$, after thresholding of the image, that thresholding making it possible to keep only the information for the pixels whereof the intensity is above a certain threshold.

Referring to the example shown in FIGS. 16 and 17, after having performed thresholding at the intensity corresponding to the value 120, it is understood that the mean intensity of the image corresponding to FIG. 17 is higher than the mean intensity of the image corresponding to FIG. 16. This is due to the fact that the histogram of FIG. 17, showing the observation of an agglutination of particles, comprises more intense pixels (gray levels higher than 200) than the histogram of FIG. 16, the latter showing the observation of a non-agglutination. The second indicator Ind2 is then for example established according to the mean intensity of the image.

According to one alternative, one determines, for each produced image, the intensity $I_{max}$, the latter corresponding, on the histogram of the image, to the highest value of the intensity bringing together a predetermined number of pixels, for example 500 pixels. One then determines the deviation between $I_{max}$ and $I_{mean}$, by subtracting $I_{max}-I_{mean}$, the second indicator Ind2 then representing that deviation. On the histogram of FIG. 17, the second indicator Ind2 thus defined is higher than in the histogram of FIG. 16. The value of the second indicator Ind2 thus determined makes it possible to conclude on the presence or absence of an agglutination phenomenon through a comparison, for example with a value $Ind2_{ref}$ obtained on a reference area, or with a predetermined value, the predetermination of that value for example being done according to experimental tests.

According to one alternative, on each transmission image, the intensity $I_{peak}$ corresponding to the maximum value of the histogram is determined, i.e., the intensity value bringing together the highest number of pixels. In FIGS. 16 and 17, this value corresponds to the peak of each distribution, respectively equal to 120 and 130. One also determines the maximum value $I_{max}$ bringing together a number of pixels with a value above a predetermined threshold. In reference to FIGS. 16 and 17, and by adopting a threshold of 500, $I_{max}$ is respectively equal to 181 and 256. The second indicator Ind2 corresponds to the distance between $I_{max}$ and $I_{peak}$, 61 for FIG. 16 and 126 for FIG. 17, respectively. One concludes on an agglutination when the second indicator Ind2 is higher, for example 25%, than a certain predetermined threshold, or when it is higher than the indicator $Ind2_{ref}$ established for the reference area.

According to one alternative, the second indicator Ind2 is a comparison indicator between a region of interest of the transmission image I and a reference image $I_{ref}$ not containing reagent (and therefore in which the agglutination does not occur), as below:

$$Ind2 = \frac{\sum_x \sum_y |I(x,y) - I_{ref}(x,y)|}{\sum_x \sum_y I(x,y) + I_{ref}(x,y)} \qquad (9)$$

The second indicator Ind2 is compared with a predetermined threshold, for example 0.25. Thus, if the second indicator Ind2 is above that threshold, an agglutination is found.

The characterization software 40 is capable of then determining an agglomeration state of the particles of the liquid 12 from the second calculated indicator Ind2.

The agglomeration state is for example determined when the second indicator Ind2 exceeds a predetermined threshold.

If the comparison is positive, i.e., if the gray level obtained is greater than the predetermined threshold, then the characterization software 40 deduces the presence of a cellular aggregation in the corresponding channel 202, 204.

In the second described embodiment, the characterization software 40 lastly determines the blood group associated with the blood sample 12 tested from the type of the first and second regions 206, 208, as well as from the table 200.

The advantages of this second embodiment are identical to those of the first embodiment previously described.

As a complement to the first embodiment, the fluid chamber 14 includes a plurality of channels, for example the two channels 202, 204 visible in FIG. 13, so as to characterize the variation of the speed of the particles of the liquid 12 when the liquid 12 is mixed with different reagents, a respective reagent then being positioned in each channel 202, 204 of the fluid chamber 14. This makes it possible, with a same device, to determine different analysis parameters of the same liquid sample, for example the coagulation time and the blood group.

Such a fluid chamber 14 is for example advantageous to characterize the coagulation of the liquid 12 containing blood, with different reagents capable of favoring the slowing of the blood particles via a coagulation of the blood, such as the different reagents 112 defined above.

One can see that the characterization system 10 according to the invention makes it possible to observe a larger part of the fluid chamber 14, while having a limited bulk.

FIGS. 18 to 29 illustrate a second example of the second embodiment, in which the liquid to be characterized 12 is a biological liquid, in particular blood or diluted blood, and the characterization system 10 is capable of characterizing the agglomeration of particles, in this case red blood cells, in the biological liquid 12.

The liquid to be characterized 12 in this example includes blood diluted at 1/20 in a PBS (Phosphate Buffered Saline) buffer, the buffer including 1% by volume of FBS (Fetal Bovine Serum).

The volume of diluted blood is 40 μL, to which a variable quantity of antibodies is added, such as an anti-red blood cell called CD235A, for example marketed by the company Becton Dickinson under reference BD 555569. The quantity of antibodies added varies from 0 to 1 μg of antibodies per μl of undiluted blood, which corresponds to a concentration comprised between 0 and 6.7 μM.

The addition of these antibodies makes it possible to mask the surface antigens of the red blood cells (in particular glycophorin A), which causes their agglutination.

The aim of this second example is to show that it is possible to characterize an agglutination state of blood particles, for example red blood cells, by lensless imaging using the characterization system 10.

For each quantity of antibodies added into the liquid to be characterized 12, the liquid sample to be characterized 12 is acquired using the characterization system 10, i.e., by lensless imaging, the obtained images 220A, 220B, 220C and 220D being visible in FIGS. 18 to 21. A grayscale histogram of the intensity of the pixels of each of these images 220A, 220B, 220C and 220D is then calculated, the calculated histograms 222A, 222B, 222C and 222D being visible in FIGS. 22 to 25. Reference images 224A, 224B, 224C and 224D of the liquid sample to be characterized 12 are also obtained with a microscope, as shown in FIGS. 26 to 29. It should be noted that, for microscopic observation, the blood sample is diluted with a dilution factor of 1/10.

In the second example, the light source 16 is a laser diode, having an emission spectrum centered on a wavelength λ for example equal to 670 nm, and the first distance D1 is substantially equal to 8 cm. The sample is confined in the fluid chamber 14 including a channel 28 with a thickness of 150 μm formed between two transparent walls with a thickness of 200 μm. These walls are made from a plastic material, for example from COP (Cyclo Olefin Polymer).

The fluid chamber 14 is directly placed on the glass cover of the matrix photodetector 20, such as a CMOS sensor, including 1280*1024 pixels, each pixel having size 5 μm×5 μm, such that the fluid chamber 14 is positioned between the CMOS sensor and the light source 16. The second distance D2 is then preferably smaller than 1 cm, for example equal to 550 μm.

The image acquisitions are for example done with an exposure time of 5 ms, with one image per acquisition. The images 220A, 220B, 220C and 220D respectively correspond to an increasing added quantity of antibodies. More specifically, the images 220A, 220B, 220C and 220D respectively correspond to:

a substantially zero quantity of antibodies, a quantity of antibodies below a threshold concentration C, a quantity of antibodies equal to the threshold concentration C, and a quantity of antibodies equal to 2 times the threshold concentration C.

When the quantity of added antibodies exceeds the threshold concentration C, the red blood cells agglomerate and the images obtained by lensless imaging using the characterization system 10 reflect the size of the agglutinates. The value of the threshold concentration C is for example equal to 250 ng of antibodies for 1 μl of undiluted blood, which corresponds to 1.7 μM.

It will be observed that the agglomeration of red blood cells causes the appearance of extended light areas (high gray level) delimited by dark areas (low gray level). This image segmentation effect into areas including several tens, or hundreds of pixels, of comparable gray levels, may be observed by comparing the images 220A (FIG. 18) or 220B (FIG. 19), in which no agglutination is observed, with the images 220C (FIG. 20) and 220D (FIG. 21), in which agglutination is observed. The presence or absence of an agglutination of particles observable in the images 220A, 220B, 220C and 220D is confirmed by the microscope observations shown in the images 224A (FIG. 26), 224B (FIG. 27), 224C (FIG. 28) and 224D (FIG. 29), respectively. This results in an evolution of the histogram of each image, the latter tending to stretch toward the low gray level values as the quantity of agglomerates increases, as shown from the histogram 222A corresponding to the image 220A toward the histogram 222D corresponding to the image 220D.

The agglutination state of the blood sample is then quantified by calculating the second indicator Ind2 according to several possible alternatives:

according to a first alternative, the second indicator Ind2 is equal to the standard deviation of the intensity distribution of the pixels of the examined area of interest, and is then denoted $Ind2_A$, according to a second alternative, the second indicator Ind2 is equal to the number of pixels below a certain threshold, that threshold for example being a fraction of the maximum gray level, divided by the total number of pixels in the examined area of interest, and the second indicator Ind2 calculated according to this second alternative is then denoted $Ind2_B$. In the example of FIGS. 22 to 25, the threshold value is equal to 125.

Table 1 below shows the value of the second indicator Ind2 according to these two alternatives and for each of the areas of interest shown in FIGS. 18 to 21.

| | FIGS. | | | |
|---|---|---|---|---|
| | 18 | 19 | 20 | 21 |
| $Ind2_A$ | 36 | 33 | 51 | 59 |
| $Ind2_B$ | $6.5 \cdot 10^{-3}$ | $6.5 \cdot 10^{-3}$ | $8.7 \cdot 10^{-2}$ | $1.4 \cdot 10^{-1}$ |

When the second indicator $Ind2_A$ according to the first alternative is below a threshold value, for example comprised between 40 and 45, there is no observable agglutination. Beyond that threshold value, the higher the value of the second indicator $Ind2_A$, the greater the quantity of agglutinated particles.

The second indicator $Ind2_B$, calculated according to the second alternative, makes it possible to reach the same conclusions, taking a threshold value comprised between $1 \cdot 10^{-2}$ and $5 \cdot 10^{-2}$.

One can see that it is possible to observe, or even quantify, an agglutination state of particles in the biological liquid 12, using an indicator calculated from an image obtained by the characterization system 10, i.e., by lensless imaging, and in particular the second indicator $Ind2_A$, $Ind2_B$, according to the first and second alternatives of this example, said second indicator depending on the distribution of the intensity of the pixels of the images 220A, 220B, 220C and 220D acquired by the characterization system 10.

The characterization system 10 can also be used in a diagnostic test based on the detection of agglutinates in a biological fluid.

FIGS. 30 to 45 illustrate a third example of the second embodiment, in which the liquid to be characterized 12 is a biological liquid, in particular blood or diluted blood, and the characterization system 10 is capable of characterizing the agglomeration, also called agglutination, of particles in the biological liquid 12.

In this third example, the detection of the agglutination of red blood cells in a blood sample is shown, including a variable quantity of A protein, the agglutination being caused by the addition of a given quantity of a reagent (an antibody).

The liquid to be characterized 12 for example includes blood diluted at 1/20 in a PBS (Phosphate Buffered Saline) buffer, the buffer including 1% by volume of FBS (Fetal Bovine Serum).

The volume of diluted blood is 40 µL, to which an antibody is incubated, such as an anti-red blood cell called CD235A, for example marketed by the company Becton Dickinson under reference BD 555569, with an A protein solution in a variable quantity. The incubation duration is 1 hour.

Thus, there are several so-called antibody—A protein solutions available, in which the antibody—A protein molar ratio is variable. The solutions may cause the agglutination of red blood cells, resulting in the name "pro-equipment solutions". A volume of 1.2 µL of each of these solutions is incubated with 40 µL of diluted blood sample described above, for 1.5 hours, each of these mixtures forming a liquid sample to be characterized 12.

In each of the mixtures thus obtained, the S antibody molar concentration is below the threshold C determined in the previous second example. In other words, this antibody concentration does not allow the spontaneous agglutination of red blood cells. In the case at hand, this concentration S is 100 ng of antibodies per µl of undiluted blood, i.e., 0.7 µM.

For each of the liquid samples to be characterized 12, an image acquisition is done using the characterization system 10, i.e., by lensless imaging, the acquired images 230A, 230B, 230C, 230D and 230E obtained being shown in FIGS. 30 to 34. A grayscale histogram of the intensity of the pixels of each of these images 230A, 230B, 230C, 230D and 230E is then calculated, the calculated histograms 232A, 232B, 232C, 232D and 232E being shown in FIGS. 35 to 39. Reference images 234A, 234B, 234C, 234D and 234E of each of the liquid samples to be characterized 12 are also obtained with a microscope, as shown in FIGS. 40 to 44. It should be noted that, for microscopic observation, the blood sample is diluted with a dilution factor of 1/10.

In this third example, the light source 16 is a laser diode, having an emission spectrum centered on a wavelength λ equal to 670 nm, and the first distance D1 is substantially equal to 8 cm. The sample is confined in the fluid chamber 14 including a channel 28 with a thickness of 150 µm formed between two transparent walls with a thickness of 200 µm. These walls are made from a plastic material, for example COP (Cyclo Olefin Polymer).

The fluid chamber 14 is directly placed on the glass cover of the matrix photodetector 20, such as a CMOS sensor. The CMOS sensor for example has a matrix of 1280 by 1024 pixels, each pixel being in the shape of a square, each side measuring 5 µm, such that the fluid chamber 14 is positioned between the CMOS sensor and the light source 16. The second distance D2 is then preferably smaller than 1 cm, for example equal to 550 µm.

The image acquisitions are for example done with an exposure time of 5 ms, with one image per acquisition. The images 230A, 230B, 230C, 230D and 230E respectively correspond to an increasing added quantity of A protein. More specifically, the images 230A, 230B, 230C, 230D and 230E respectively correspond to:
- absence of antibodies, i.e., an Antibody:A Protein molar ratio=0:40 (0 antibody molecules for 40 A protein molecules),
- absence of A protein, i.e., an Antibody—A Protein molar ratio=1:0 (1 antibody molecule for 0 A protein molecules),
- Antibody:A Protein molar ratio=1:1 (1 antibody molecule for 1 A protein molecule),
- Antibody:A Protein molar ratio=1:5 (1 antibody molecule for 5 A protein molecules), and
- Antibody:A Protein molar ratio=1:40 (1 antibody molecule for 40 A protein molecules).

The antibody here serves as a binding agent between an A protein molecule and a red blood cell, as will be outlined later.

Figure 30:
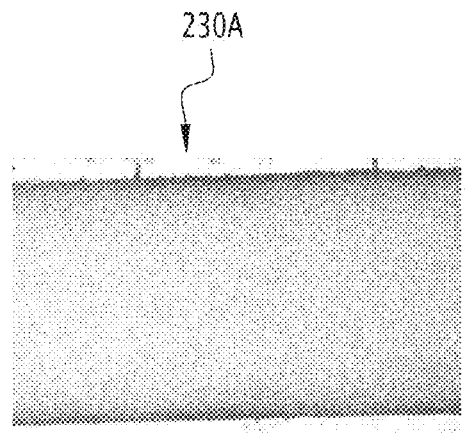
FIGS. 30 to 34 are images of the liquid to be characterized, acquired by the photodetector according to a third example of the second embodiment, the liquid to be characterized containing blood, a variable quantity of A protein, and a same added quantity of antibodies.
Figure 31:
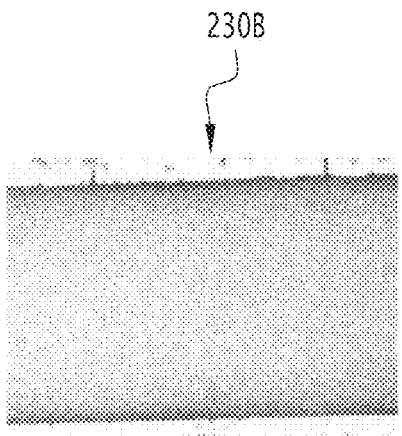

In the presence of A protein and in the absence of antibodies, no red blood cell agglutination is observed, as shown in FIG. 30. In the presence of antibodies and the absence of A protein, no red blood cell agglutination is observed, which is shown in FIG. 31.

Figure 32:
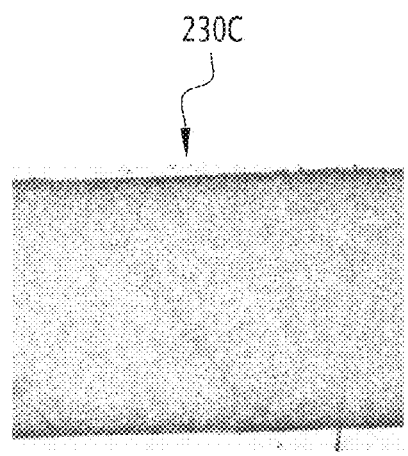

When the antibody:A protein ratio is equal to 1:1, there is also no observed red blood cell agglutination, as shown in FIG. 32.

Figure 33:
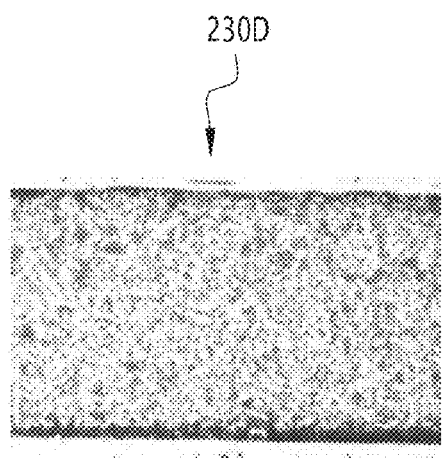
Figure 34:
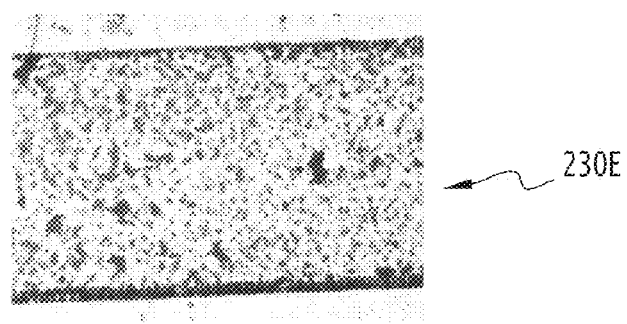
Figure 35:
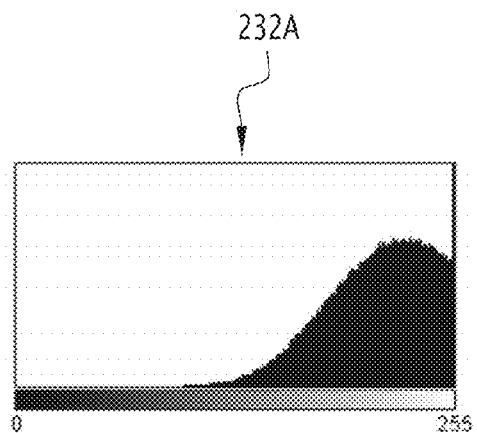
FIGS. 35 to 39 are histograms of the gray level of the images acquired in FIGS. 30 to 34, respectively.
Figure 36:
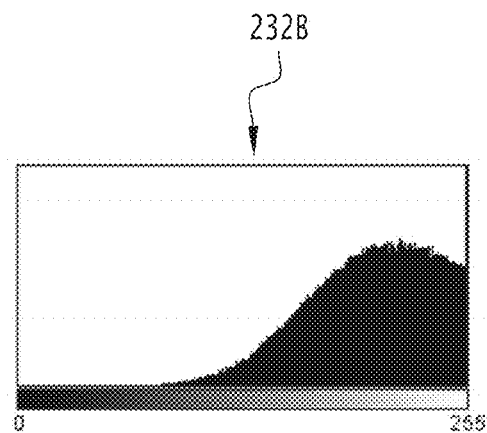
Figure 37:
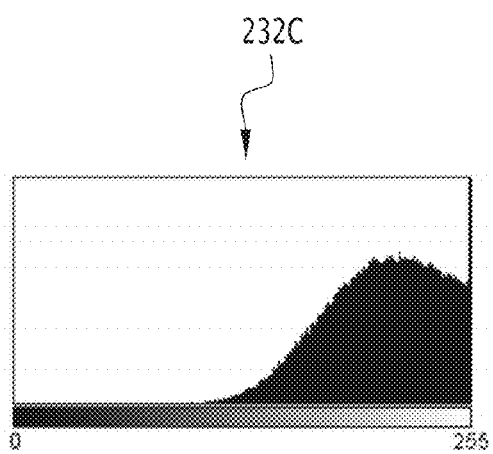
Figure 38:
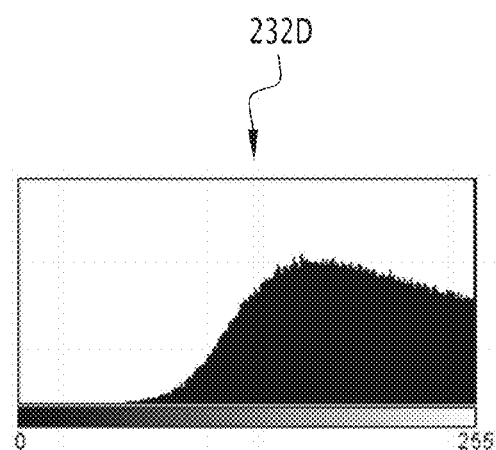
Figure 39:
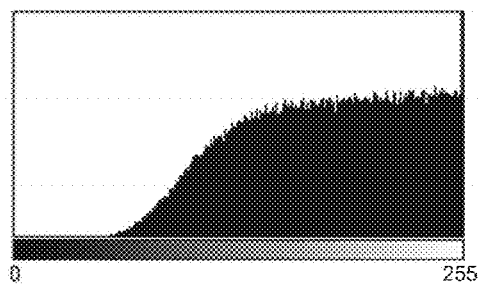

When the antibody:A protein ratio is equal to 1:5, red blood cell agglutination is observed, shown in FIG. 33. When the antibody:A protein ratio is equal to 1:40, red blood cell agglutination is also observed, shown in FIG. 34, the size of the agglutinates observed in FIG. 34 being larger than that of the agglutinates observed in FIG. 33.

FIGS. 35 to 39 show the histogram of the intensity of the pixels of FIGS. 30 to 34, respectively.

One can see that the agglomeration of red blood cells causes the appearance of light areas (high gray level) delimited by a dark area (low gray level). This image segmentation effect into areas including several tens, or hundreds of pixels, of comparable gray levels, may be observed by comparing the images 230A (FIG. 30) or 230B (FIG. 31) or 230C (FIG. 32), in which no agglutination is observed, with images 230D (FIG. 33) and 230E (FIG. 34), in which agglutination is observed. The presence or absence of an agglutination of particles observable in the images 230A, 230B, 230C, 230D and 230E is confirmed by the microscope observations shown in the images 234A (FIG. 40), 234B (FIG. 41), 234C (FIG. 42), 234D (FIG. 43) and 234E (FIG. 44), respectively. This results in an evolution of the histogram of each image, the latter tending to stretch toward the low gray level values as the quantity of agglomerates increases, as shown from the histogram 232A corresponding to the image 230A toward the histogram 232E corresponding to the image 230E. The agglutination state of the blood sample is then quantified by calculating the second indicator Ind2 according to several possible alternatives:

according to a first alternative, the second indicator Ind2 is equal to the standard deviation of the intensity distribution of the pixels of the examined area of interest, and is then denoted $Ind2_A$, according to a second alternative, the second indicator Ind2 is equal to the number of pixels below a certain threshold, that threshold for example being a fraction of the maximum gray level, divided by the total number of pixels in the examined area of interest, and the second indicator Ind2 calculated according to this second alternative is then denoted $Ind2_B$. In the example of FIGS. 22 to 25, the threshold value is equal to 125.

Table 2 below shows the value of the second indicator Ind2 according to these two alternatives and for each of the areas of interest shown in FIGS. 30 to 34.

| | FIGS. | | | | |
|---|---|---|---|---|---|
| | 30 | 31 | 32 | 33 | 34 |
| $Ind2_A$ | 33 | 39 | 35 | 50 | 52 |
| $Ind2_B$ | $4.0\ 10^{-3}$ | $1.5\ 10^{-2}$ | $5.5\ 10^{-3}$ | $6.5\ 10^{-2}$ | $9.5\ 10^{-2}$ |

When the second indicator $Ind2_A$ according to the first alternative is below a threshold value, for example comprised between 40 and 45, there is no observable agglutination. Beyond that threshold value, the higher the value of the second indicator $Ind2_A$, the greater the quantity of agglutinated particles.

The second indicator $Ind2_B$, calculated according to the second alternative, makes it possible to arrive at the same conclusions, using a threshold value comprised between $1\ 10^{-2}$ and $5\ 10^{-2}$.

One can thus see that it is possible to observe, or even quantify, an agglutination state of particles in the biological liquid 12, using an indicator calculated from an image obtained by the characterization system 10, i.e., by lensless imaging, and in particular the second indicator $Ind2_A$, $Ind2_B$, according to the first and second alternatives of this example, which depends on the distribution of the intensity of the pixels of the images 230A, 230B, 230C, 230D and 230E acquired by the characterization system 10.

Furthermore, the greater the quantity of A protein, the larger the size of the agglutinates, the quantity of antibodies added being constant. Thus, the second indicator $Ind2_A$, $Ind2_B$ quantifying the agglutination state may also quantify a quantity of protein in the blood sample.

Depending on the antibody-A protein molar ratio, the red blood cells agglomerate and the images 230A, 230B, 230C, 230D and 230E obtained by lensless imaging reflect the size of the agglutinates, i.e., the degree of agglutination. It is then understood that by introducing a predetermined quantity of antibodies into the blood sample, it is possible to estimate the quantity of A protein present in that sample according to the agglutination state, i.e., according to the second indicator $Ind2_A$, $Ind2_B$ previously described.

In other words, the quantity of A protein beyond which agglutination is observed constitutes the detection limit for assaying that protein in a blood sample, by introducing a given quantity of antibodies into the liquid sample to be characterized 12.

Thus, one will understand that it is possible to observe, or even quantify, an agglutination state of particles in a biological fluid, using indicators relative to the image obtained by lensless imaging, and in particular the second indicator $Ind2_A$, $Ind2_B$, according to the first and second alternatives of this second example, which depends on the distribution of the intensity of the pixels. This agglutination state for example depends on the concentration of an analyte in the biological liquid, the quantification of that agglutination state then making it possible to assay that analyte in the liquid. The example shows that that assay can be done by introducing a bifunctional reagent, in this case the antibody 300, into a blood sample, capable of binding both a particle of the biological fluid, in this case the red blood cells 302, and the analyte to be assayed, in this case the A protein 304, thereby forming a bridge between an analyte 304 and the red blood cells 302, as shown in FIG. 45.

The term bifunctional designates the ability of the reagent to bind both to a particle and to an analyte.

In general, the term "analyte" refers to a chemical or biological species present in the liquid, such as a molecule, a macromolecule (for example, protein or nucleic acid), a cell, a bacteria, a virus, or spore.

Figure 45:
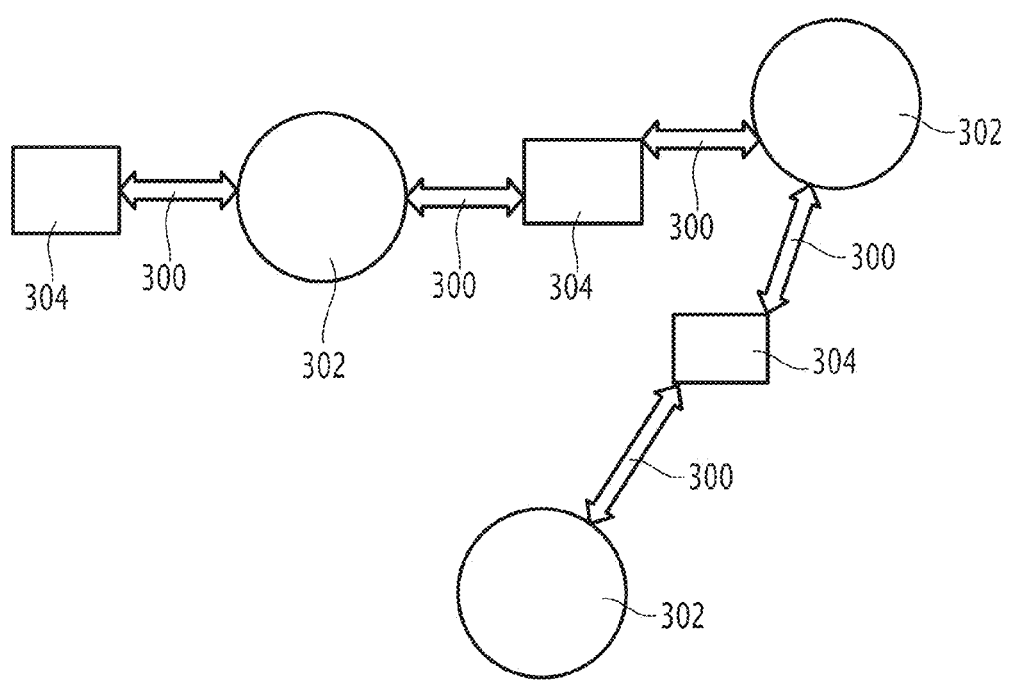
FIG. 45 is a very diagrammatic illustration of the agglutination of the red blood cells and A proteins using antibodies.

Furthermore, the analyte 304 must include at least two binding sites with the bifunctional reagent, as shown in FIG. 45. Thus, each analyte 304 may be bind, via the bifunctional reagent, to at least two particles. This causes agglutination of the particles.

In other words, the agglutination state of the particles in the liquid 12 depends on the quantity of analyte present in the liquid 12, that quantity being able to be assayed by adding a reagent capable of causing the formation of agglutinates, the reagent 300 then being able to bind between one of said particles 302 and an analyte 304 so as to form an agglutinate.

As a function of the quantity of analyte 304 present in the liquid, an agglutinate is formed, made up of particles 302 and analytes 304. By determining the agglutination state corresponding to a given quantity of introduced reagent, it is then possible to estimate the quantity of analyte 304 present in the liquid 12.

In the second and third examples of the second embodiment, previously described, the second distance D2 is smaller than 1 cm. The inventors nevertheless also observed that, in the case of the characterization of agglutination, values of the second distance D2 greater than 1 cm, such as values of several centimeters, or even several tens of centimeters, do make it possible to obtain usable results, although values of the second distance D2 below 1 cm remain preferable.

In general, these second and third examples demonstrate another aspect of the invention. According to this other aspect, the invention relates to a method for characterizing the agglutination of particles, such as biological particles, in a liquid, for example a biological liquid, and in particular a bodily fluid, the characterization method including the following steps:

introducing liquid into a fluid chamber, lighting the fluid chamber using a light beam, the light beam in particular coming from a light source, such as a laser diode or a light-emitting diode, acquiring an image, or a plurality of images, of the fluid chamber using a matrix photodetector, the photodetector preferably being placed at a distance from the fluid chamber of less than 1 cm, the fluid chamber being positioned between the light source and the matrix photodetector.

processing the image, or the plurality of images, to determine an indicator characterizing the agglutination of particles in the biological liquid, and characterizing the agglutination of particles in the liquid, depending on the value of the indicator.

It should be noted that the image is acquired by the photodetector, preferably without a magnifying lens between the fluid chamber and the matrix photodetector. However, objective microlenses may be provided at each pixel of the detector, as previously stated.

Additionally and optionally, the indicator is an indicator representing the distribution of the intensity of the pixels in an image, or more generally, any other indicator translating the segmentation of the image into different areas, each area including several tens to hundreds of pixels of comparable intensity, i.e., where the intensity is distributed in a range of gray levels of approximately half, or even one third, or even one quarter, or even less than one quarter of the dynamic of the image.

Additionally and optionally, the characterization method includes the addition of a reagent, which can cause the agglutination of particles in the liquid.

As illustrated in the third example of the second embodiment, agglutination of the particles for example depends on a quantity of analyte present in the liquid.

According to this alternative, the invention relates to a method for detecting the quantity of an analyte in a liquid, for example a biological liquid, and in particular a bodily fluid, the detection method including the following steps:

introducing liquid into a fluid chamber, lighting the fluid chamber using a light beam, the light beam in particular coming from a light source, such as a laser diode or a light-emitting diode, adding a reagent, capable of causing the formation of agglutinates of particles and analytes in the liquid, acquiring an image, or a plurality of images, of the fluid chamber using a matrix photodetector, the photodetector preferably being placed at a distance from the fluid chamber of less than 1 cm, the fluid chamber being positioned between the light source and the matrix photodetector, processing the image, or the plurality of images, to determine an indicator characterizing the agglutination of particles in the biological liquid, and estimating the quantity of analyte in the liquid, as a function of the value of the indicator.

According to still another aspect, the invention relates to a method for determining a parameter of the liquid 12, including blood, the method including the following steps:

introducing the liquid 12 in the fluid chamber 14, lighting the fluid chamber 14 using the excitation laser beam 18 emitted by the light source 16, the laser beam 18 extending through the fluid chamber 14 in the longitudinal direction X, acquiring at least one image $I_n(x,y)$, $I_{n+m}(x,y)$, $I(x,y)$ using the matrix photodetector 20, the image $I_n(x,y)$, $I_{n+m}(x,y)$, $I(x,y)$ being formed by radiation transmitted by the lighted fluid chamber 14, and determining an indicator $Ind1_{n,n+m}$, $Ind2$, from said at least one image $I_n(x,y)$, $I_{n+m}(x,y)$, $I(x,y)$.

During the acquisition step, the photodetector 20 is positioned at the distance D2, smaller than 1 cm, from the fluid chamber 14 in the longitudinal direction X.

As a complement and optionally, the determination method comprises one or more of the following features, considered alone or according to all technically possible combinations:

the light beam 18 directly lights the fluid chamber 14, and the image $I_n(x,y)$, $I_{n+m}(x,y)$, $I(x,y)$ is formed directly by the radiation transmitted by the lighted fluid chamber 14, in the absence of a magnification lens positioned between the fluid chamber 14 and the photodetector 20;

the parameter is a coagulation, and the method then includes the following steps:

mixing the liquid 12 with a reagent to favor the coagulation of the blood, acquiring a series of transmission images $I_n(x,y)$, $I_{n+m}(x,y)$ at different moments n, n+m, calculating an indicator $Ind1_{n,n+m}$ to establish a correlation between two areas of the transmission images $I_n(x,y)$, $I_{n+m}(x,y)$, the coagulation being determined as a function of the value of said indicator;

the parameter is a coagulation time, and the method then includes the following steps:

mixing the liquid 12 with a reagent to favor the coagulation of the blood, acquiring a series of transmission images $I_n(x,y)$, $I_{n+m}(x,y)$ at different moments n, n+m, calculating an indicator $Ind1_{n,n+m}$ to establish a correlation between two images $I_n(x,y)$, $I_{n+m}(x,y)$, and determining a time interval, called coagulation time, between an initial moment t0 and the moment $t2_A$, $t2_B$ at which the indicator $Ind1_{n,n+m}$ takes a predetermined value.

The parameter is an agglutination of blood particles, and the method then includes the following steps:

mixing the liquid 12 with a reagent capable of creating an agglutination of the blood particles, acquiring a transmission image $I(x,y)$, calculating an indicator Ind2 as a function of the intensity in a predetermined area of the transmission image $I(x,y)$, and determining an agglutination state when that indicator Ind2 exceeds a predetermined threshold;

the blood particles are red blood cells, the reagent including an antibody, the agglutination state then providing information relative to the blood group.

According to this other independent aspect, the invention also relates to a system for determining a parameter of the liquid 12, including blood, the determination system comprising:

the fluid chamber 14 designed to receive the liquid 12;

the light source 16 capable of emitting the excitation laser beam 18 to light the fluid chamber 14, the laser beam 18 extending the longitudinal direction X;

the matrix photodetector 20 capable of acquiring at least one image $I_n(x,y)$, $I_{n,n+m}(x,y)$, $I(x,y)$ of a radiation transmitted by the lighted fluid chamber 14; and the information processing unit 21 including means for determining an indicator $Ind1_{n,n+m}$, Ind2, from said at least one image $I_n(x,y)$, $I_{n+m}(x,y)$, $I(x,y)$.

The photodetector 20 is positioned at the distance D2, smaller than 1 cm, from the fluid chamber 14 in the longitudinal direction X.

The parameter is a coagulation, coagulation time, or an agglutination of blood particles.

According to a third embodiment, which corresponds to another independent aspect, the system 10 according to the invention is a system for estimating the quantity of the analyte 304 contained in the liquid 12.

According to this third embodiment, the system 10 comprises the fluid chamber 14 configured for receiving the liquid 12 and for mixing the liquid 12 with the bifunctional reagent 300, also called bi-specific reagent, the bi-specific reagent 300 being configured for grafting on both the particle 302 and the analyte 304 present in the liquid 12, as shown in FIG. 45.

The system 10 further comprises the light source 16 configured for emitting the excitation beam 18 to illuminate the fluid chamber 14, the beam 18 propagating through the fluid chamber 14.

The system 10 further comprises the matrix photodetector 20 configured for acquiring at least one image of a radiation transmitted by the lighted fluid chamber 14 and the information processing unit 21.

The information processing unit 21, as shown in FIG. 1, includes the data processor 30 and the memory 32, and the memory is further adapted to store an estimation software 350 configured for estimating, from at least one acquired image In, the quantity of said analyte 304 in the liquid 12.

The information processing unit 21 is therefore configured for estimating, from at least one acquired image In, the quantity of said analyte 304 in the liquid 12.

The estimation software 350, when executed by the data processor 30, forms an estimation module for estimating said analyte quantity.

Alternatively, the estimation module 350 is made in the form of a programmable logic component or in the form of a dedicated integrated circuit.

The term bifunctional, or bi-specific, designates the ability of the reagent 300 to bind both to a particle 302 and to an analyte 304. In other words, the bi-specific reagent 300 is configured for grafting to both the particle 302 and the analyte 304 within the liquid 12.

In general, the term "analyte" refers to a chemical or biological species present in the liquid, such as a molecule, a macromolecule (for example, protein or nucleic acid), a cell, a bacteria, a virus, or spore.

Furthermore, the analyte 304 must include at least two binding sites with the bifunctional reagent 300, as shown in FIG. 45. These binding sites are located on different places within or on the analyte 304.

Thus, each analyte 304 may be bound, via the bifunctional reagent 300, to at least two particles 302. This gives rise to the agglutination of particles 302.

In the example of FIGS. 47 to 55, the analyte 304 is a D-dimer. In other words, the analyte 304 is a small protein fragment present in the blood after a blood clot is degraded by fibrinolysis. The analyte 304 is therefore a fibrin degradation product, also noted FDP.

In the example of FIGS. 47 to 55, the particles 302 are blood particles, in particular red blood cells.

In the example of FIGS. 47 to 55, the bi-specific reagent 300 is therefore configured to be grafted on both a blood particle, in particular red blood cells, and the analyte 304 present in the liquid, in particular the D-dimer.

When the bi-specific reagent 300 is configured to bind to the red blood cells on one hand and to the D-dimer on the other hand, the bi-specific reagent 300 is for example prepared from fragments of monoclonal antibodies. A first monoclonal antibody is, for example, RAT-1C3/86 and is adapted to bind to human red blood cells, and the second monoclonal antibody is, for example, DD-3B6/22 and is adapted to bind to the D-dimer.

Both the bi-specific reagent 300 and the D-dimer are, for example contained in a kit, such as the so-called SimpliRED D-dimer kit sold by BBI™ Solutions. The SimpliRED D-dimer kit is a whole blood agglutination assay for the identification of D-dimer. In said kit, bi-specific reagent 300 is a conjugate of D-dimer specific monoclonal antibody that binds to the D-dimer 304 joined to a monoclonal antibody that binds to the outside of red blood cells 302. When this bi-specific reagent 300 is mixed with patient blood, agglutination of the red blood cells 302 will occur if the blood sample contains D-dimers. The higher the D-dimer concentration is, the greater the agglutination. In the absence of D-dimer, no agglutination takes place.

The SimpliRED D-dimer kit contains the aforementioned bi-specific reagent 300, a positive control and a negative control. The positive control is a solution containing human D-dimer and the negative control is a solution that does not contain D-dimer.

The estimation module 350 is configured for estimating, from at least one acquired image In, the quantity of the analyte 304 in the liquid 12. The estimation module 350 is further configured for calculating a third indicator $Ind_3$ for each acquired image, the third indicator $Ind_3$ being representative of the intensity of the pixels of the image in a region of the image In. The analyte 304 in the liquid 12 is then estimated by estimation module 350 according to the third indicator $Ind_3$.

Figure 46:
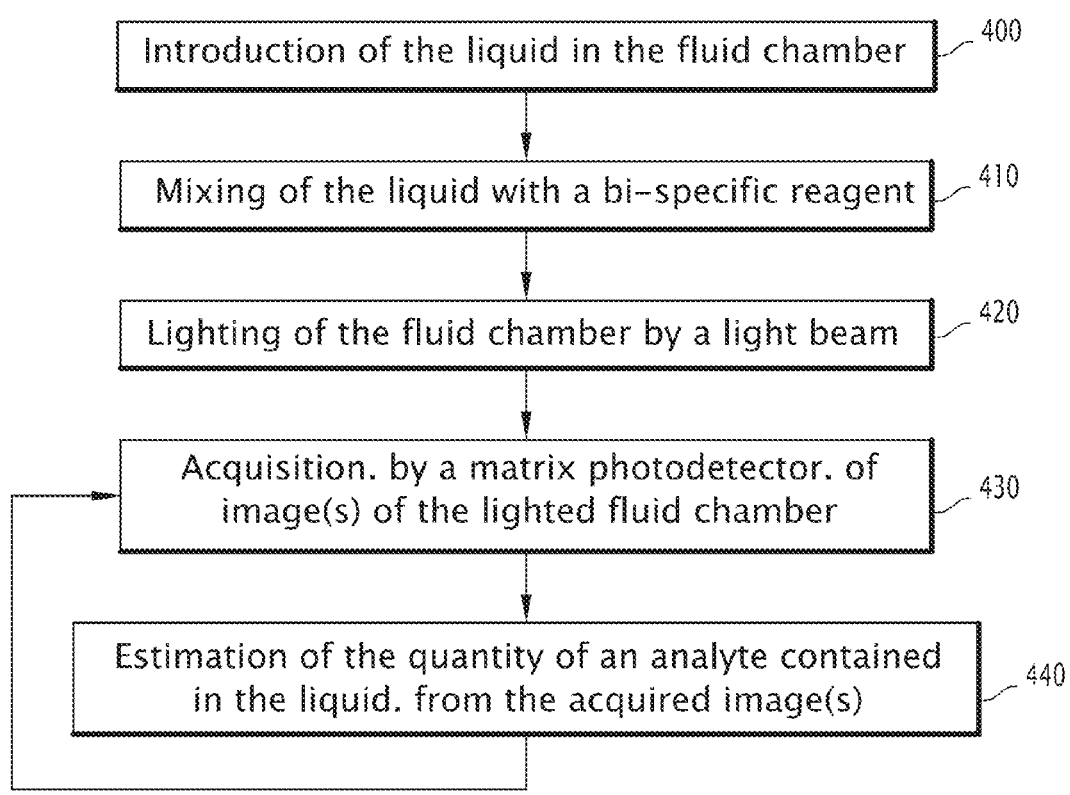
FIG. 46 is a flowchart of an estimation method according to the invention.

The operation of the third embodiment will now be described in view of FIGS. 46 to 55, in particular in view of the flowchart of FIG. 46.

During the initial step 400, the liquid 12, for example the blood sample of a patient, is introduced into the fluid chamber 14.

The liquid 12 is then mixed with the bi-specific reagent 300 during step 410. The mixing between the liquid 12 and the bi-specific reagent 300 occurs when the liquid 12 gets into contact with the bi-specific reagent 300.

Depending on the concentration of the analyte 304 in the liquid 12, for example of D-dimer in the liquid 12, a cellular agglutination can be observed in the fluid chamber 14.

The liquid 12, such as the blood sample, mixed with the bi-specific reagent 300, is then illuminated by the light beam 18 during step 420.

During step 430, the matrix photodetector 20 acquires a transmission image $I(x,y)$ including part of the fluid chamber 14.

One skilled in the art will observe that, according to the third embodiment, the acquisition of a single transmission image $I(x,y)$ makes it possible to characterize the agglutination level of the particles within the liquid 12. It is then possible to process said transmission $I(x,y)$ so as to get information about the concentration of the analyte 304 within the blood.

As previously indicated, the absence of a magnification lens between the fluid and the photodetector 20, coupled with the significant surface of the incident beam, makes it possible to form a usable image at a short distance, covering a large field of view, for example several millimeters squared.

During the acquisition step 430, the photodetector 20 is preferably placed near the fluid chamber 14, the second distance D2 between the fluid chamber 14 and the photodetector 20 in the longitudinal direction X being preferably smaller than 1 cm.

At the end of the acquisition step 430, the estimation software 350 provides, during step 440, an estimation of the quantity of the analyte 304 within the liquid 12.

The estimation step 440 further includes a step of calculating the third indicator $Ind_3$ for each acquired image In, and the quantity of the analyte 304 contained in the liquid 12 is then derived from said indicator $Ind_3$.

During the estimation step 440, a histogram 450, as shown in FIGS. 48, 50, 52 and 54, is computed for a region of interest in each acquired image In. Each histogram 450 plots the number of pixels as a function of intensity range.

The calculated indicator $Ind_3$ depends on the computed histogram 450.

As it will described in detail hereinafter, each histogram 450 includes at least one peak, a darkest peak 460 corresponding to the lowest intensity values.

The third indicator $Ind_3$ is, for example, a function of the most represented intensity value 470 of the darkest peak 460, as shown in FIGS. 48, 50, 52 and 54.

Figure 55:
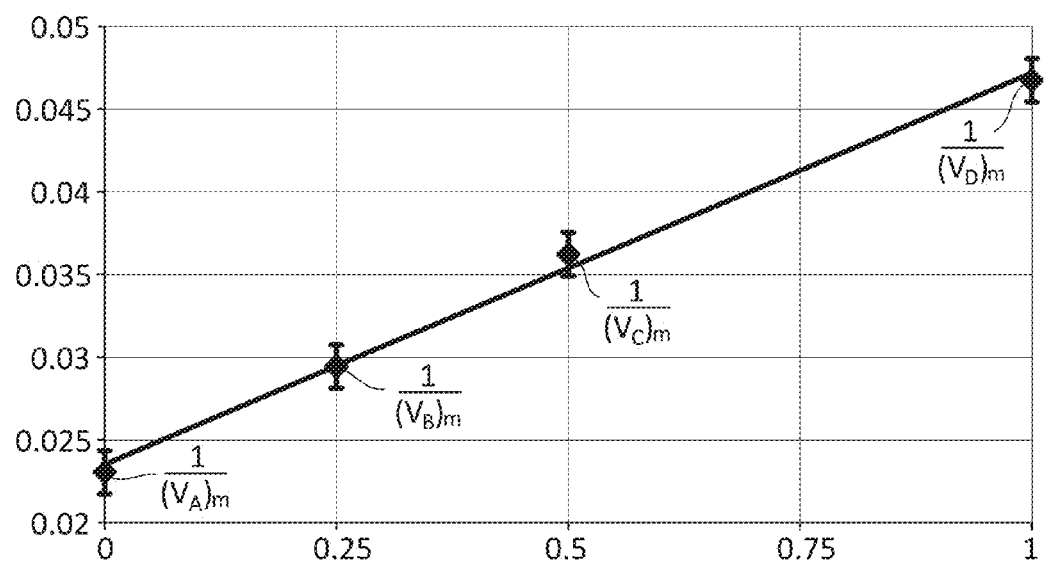
FIG. 55 is a view of an inverse of the most represented intensity value of the darkest peak in the histograms of FIGS. 48, 50, 52 and 54, as a function of the different values of the D-dimer concentration.

More precisely, the estimated quantity of the analyte 304 depends on the inverse of the most represented intensity value 470 of the darkest peak, as it will described in further detail in view of FIG. 55.

Figure 50:
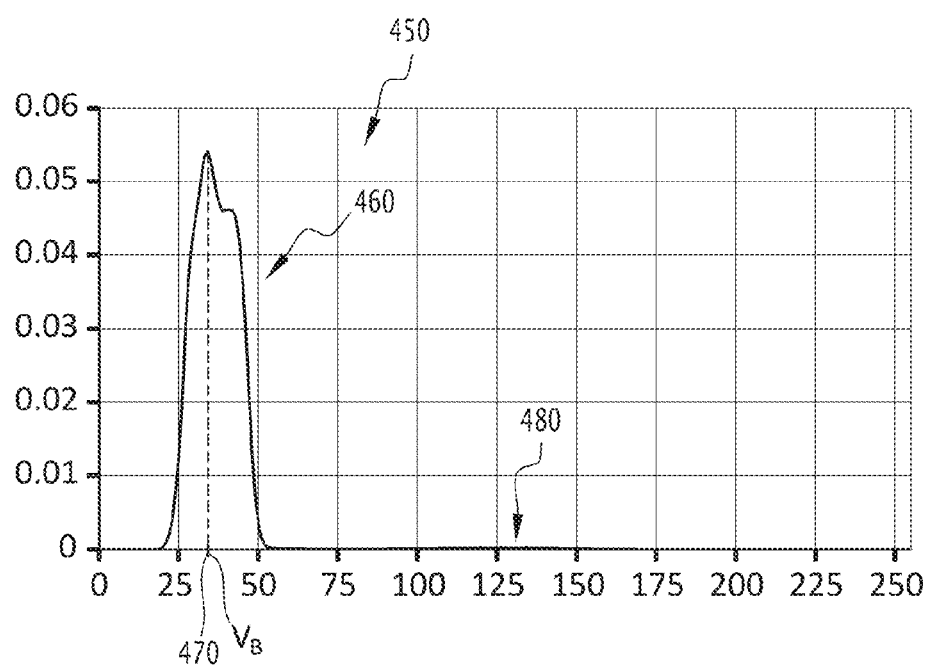
Figure 52:
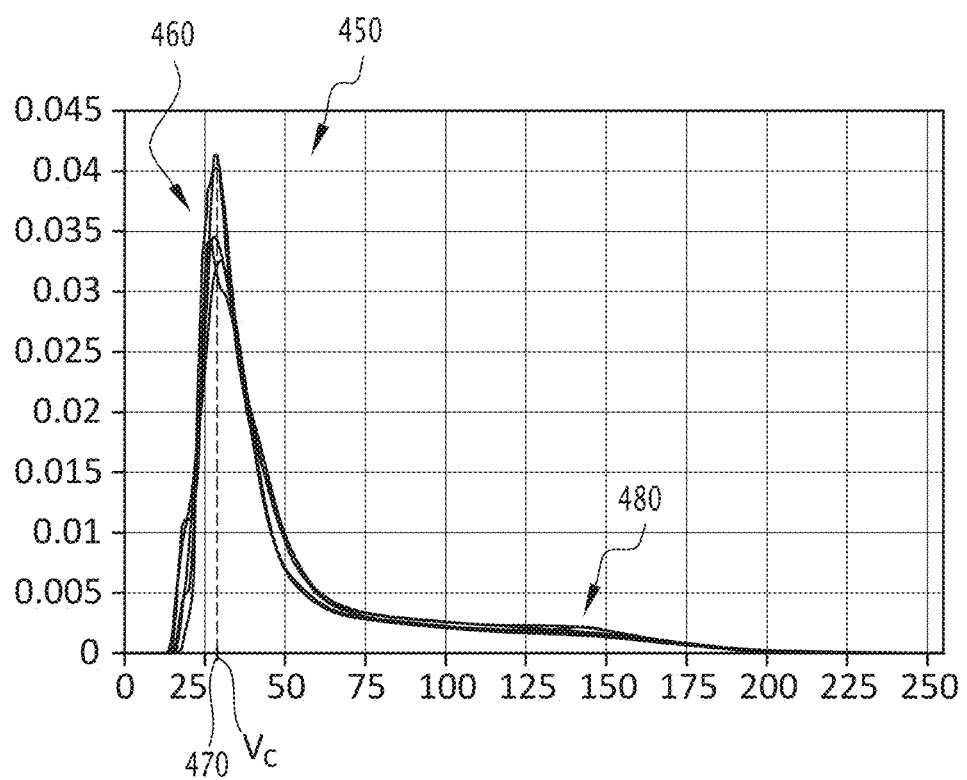
Figure 54:
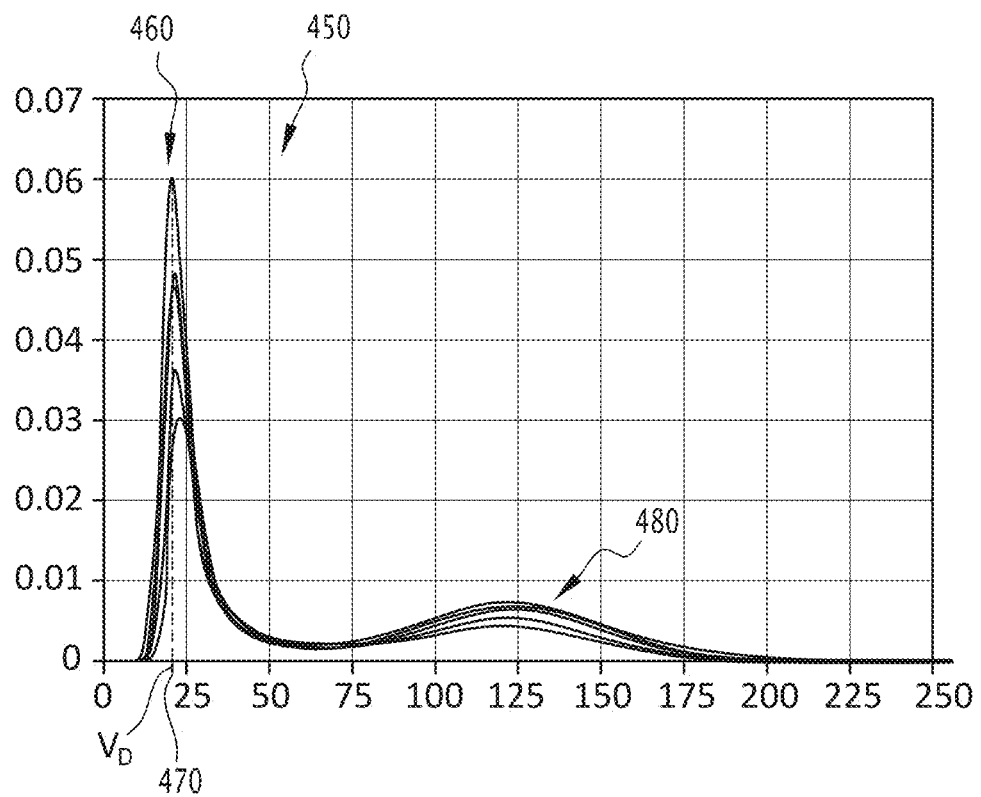

In addition, above a given analyte concentration, said histogram 450 may include two peaks 460, 480: a first peak 460 being the darkest peak corresponding to the lowest intensity values, and a second peak 480 corresponding to intensity values greater than the intensity values of the first peak 460, as shown in FIGS. 50, 52 and 54.

Alternatively, third indicator $Ind_3$ is a function of the number of pixels within the second peak 480.

The results obtained for different quantities of analyte 304 in the liquid will now be described in view of the example of FIGS. 47 to 55. In this example, the analyte 304 is D-dimer and this test was conducted using the SimpliRED D-dimer kit.

Initially, the positive control of the SimpliRED D-dimer kit is diluted, for example with the negative control, in order to obtain various concentrations of the D-Dimer, for example the concentrations being respectively $0 \times C_0$, $0.25 \times C_0$, $0.5 \times C_0$ and $1 \times C_0$, $C_0$ being the concentration of D-dimer in the positive control.

Thereby, four solutions are obtained, each one containing different concentrations of analyte 304:
- the first solution is the negative control, in other words corresponds to a sample without D-dimer;
- the second solution includes analytes 304 with a concentration of $0.25 \times C_0$;
- the third solution includes analytes 304 with a concentration of $0.5 \times C_0$; and
- the fourth solution includes analytes 304 with a concentration of $1 \times C_0$.

Four samples $12_1$, $12_2$, $12_3$ and $12_4$ are then prepared, by adding, to 3.5 μL of one of these solutions 1.45 μL of blood and 3.5 μL of the bi-specific reagent 300.

FIGS. 47, 49, 51 and 53 respectively illustrate images acquired by the matrix photodetector 20 of the samples $12_1$, $12_2$, $12_3$ and $12_4$.

Figure 47:
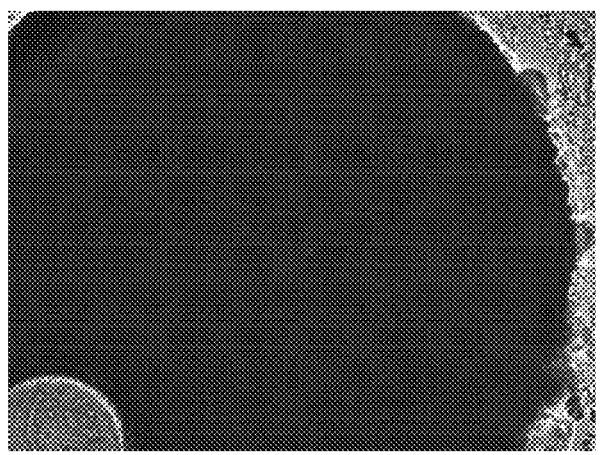
FIGS. 47, 49, 51 and 53 are images of the chamber containing a liquid including blood and mixed with a bi-specific reagent, for different values of the concentration of a D-dimer in said liquid, said images being acquired by the photodetector.
Figure 49:
Figure 51:
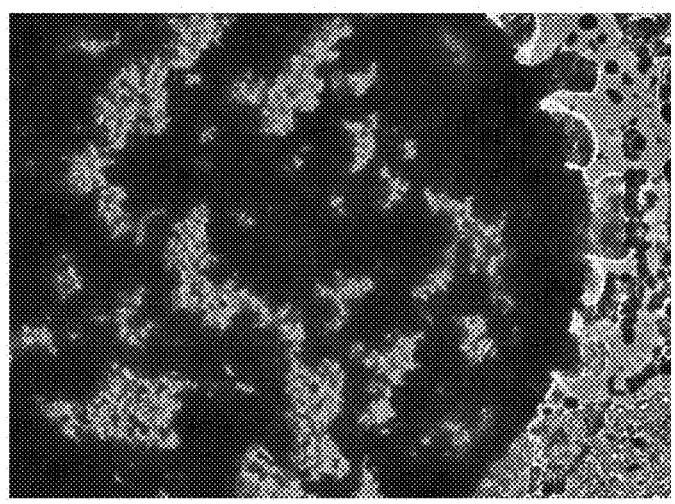

More precisely, FIG. 47 displays an acquired image for the first sample $12_1$ without D-dimer, FIGS. 49, 51 and respectively 53, respectively display the acquired image for the second sample $12_2$ (D dimer concentration of $0.25 \times C_0$), the third sample $12_3$ (D dimer concentration of $0.5 \times C_0$), and the fourth sample $12_4$ (D dimer concentration of $1 \times C_0$).

Figure 48:
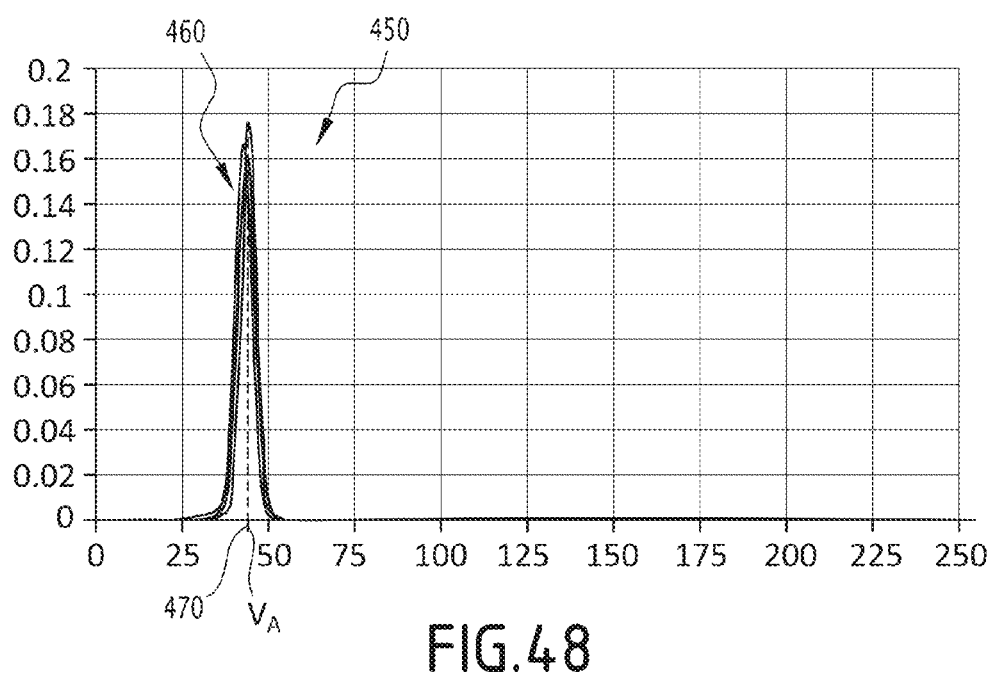
FIGS. 48, 50, 52 and 54 are histograms corresponding to the FIGS. 47, 49, 51 and 53, each histogram representing the number of pixels for each intensity value in the corresponding acquired image.

FIG. 48 illustrates the histogram 450 of a region of interest (ROI) of the FIG. 47, with respect to the first sample $12_1$. The darkest peak is centered on a grey level value $V_A$ of 43. FIG. 50, illustrates the histogram 450 of a region of interest (ROI) of the FIG. 49, with respect to the first sample $12_2$. The darkest peak is centered on a grey level value $V_B$ of 34.

FIG. 52, illustrates the histogram 450 of a region of interest (ROI) of the FIG. 51, with respect to the first sample $12_3$. The darkest peak is centered on a grey level value $V_C$ of 26.

Figure 53:
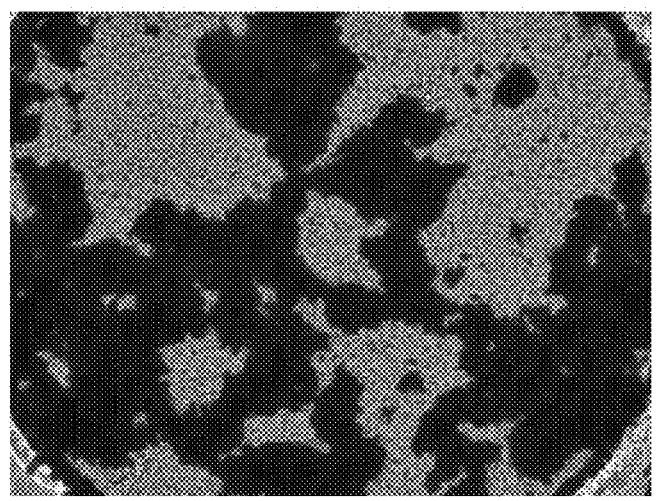

FIG. 54, illustrates the histogram 450 of a region of interest (ROI) of the FIG. 53, with respect to the first sample $12_4$. The darkest peak is centered on a grey level value $V_D$ of 20.

Other images were acquired of the first, third and fourth samples $12_1$, $12_2$, $12_3$, $12_4$ leading to the following table:

| D-dimer concentration | Darkest peak graylevel | | | | | Mean of darkest peak graylevel | 1/(Mean of darkest peak graylevel) |
|---|---|---|---|---|---|---|---|
| $0 \times C_0$ | 43 | 43 | 44 | | | $43.3 = (V_A)_m$ | $0.0230 = 1/(V_A)_m$ |
| $0.25 \times C_0$ | 34 | | | | | $34 = (V_B)_m$ | $0.0294 = 1/(V_B)_m$ |
| $0.5 \times C_0$ | 26 | 29 | 29 | 28 | 26 | $27.6 = (V_C)_m$ | $0.0362 = 1/(V_C)_m$ |
| $1 \times C_0$ | 20 | 21 | 21 | 22 | 23 | $21.4 = (V_D)_m$ | $0.0467 = 1/(V_D)_m$ |

This table summarizes the mean value $(V_A)_m$, $(V_B)_m$, $(V_C)_m$, $(V_D)_m$ of the grey level $(V_A)$, $(V_B)$, $(V_C)$, $(V_D)$, with respect to samples $12_1$, $12_2$, $12_3$, $12_4$ respectively.

Then, in FIG. 55, the inverse of a mean of the values $V_A$, $V_B$, $V_D$ and $V_D$, said means being respectively referenced $(V_A)_m$, $(V_B)_m$, $(V_C)_m$, and $(V_D)_m$, are plotted as a function of the D-dimer concentration (with a concentration equal to 0 for the first liquid 12 without D-dimer). It can be seen that these values define substantially a linear relation, according to the following equation:

$$y \approx 0.0237 \cdot x + 0.0235 \qquad (10)$$

Accordingly, the third indicator $Ind_3$ can be derived as the inverse of a mean of the most represented intensity value 470 of the darkest peak 460. The mean is any kind of well-known means, for example an arithmetic mean.

Alternatively, the third indicator $Ind_3$ is a function of the number of pixels within the second peak 480. Indeed, as can be seen in FIGS. 48, 50, 52 and 54, the number of pixels within the second peak 480 increases when the D-dimer concentration increases as well. The number of pixels within the second peak 480 in FIG. 54 (sample $12_4$) is accordingly higher than said number of pixels within the second peak 480 in FIG. 52 (sample $12_3$), which is itself higher than said number of pixels within the second peak 480 in FIG. 50 (sample $12_2$). Finally, in FIG. 48, corresponding to the sample $12_1$ (no D-dimer), there is a single peak 460 and no second peak is visible.

Thus, one will understand that it is possible to monitor, and furthermore to precisely quantify, the concentration of the analyte 304, such as D-dimer in the biological sample 12, using an indicator derived from the image obtained by imaging, and more particularly using the third indicator $Ind_3$.

The indicator $Ind_3$ is related to an agglutination state which itself depends on the concentration of the analyte 304 in the biological liquid 12. The quantification of that agglutination state via lensless imaging allows assaying said analyte 304 in a corresponding sample 12, and in particular estimating the D-dimer concentration in a corresponding blood sample 12. This example shows that that assay can be done by introducing the bi-specific reagent 300 into the blood sample 12, the bi-specific reagent 300 being configured for binding both on a particle of the biological sample 12, in this case the red blood cells 302, and on the analyte 304 to be assayed, in this case the D-dimer, thereby forming a bridge between the analyte 304 and the red blood cells 302, as shown in FIG. 45.

Thus, the agglutination state of the particles in the liquid 12 depends on the concentration of analyte within the liquid 12. This concentration can be monitored by adding a reagent capable of causing the formation of agglutinates, by binding said particles 302 and said analyte 304.

Depending on the concentration of analyte 304 within the liquid 12, an agglutinate is formed, involving particles 302 and analytes 304. By determining the indicator Ind3 which depends on the agglutination state it is then possible to estimate the concentration of analyte 304 present in the sample 12.

Thus, the ability of the system 10 to detect D-dimer, and more precisely to estimate the quantity of D-dimer in the blood, is possible, due to the agglutination, by means of the interaction of the bi-specific reagent, the red blood cells and the D dimer proteins.

The estimation system 10 according to this third embodiment therefore allows detecting D-dimers, i.e. fibrin degradation products, in the blood and furthermore allows estimating the concentration of D-dimers in blood.

The method and system according to the invention allow the detection and assessment of an agglutination level invisible for the naked eye. In addition, this sensitivity of the device is high, which may give rise to low level detection of D-dimers. While this specific embodiment focuses on D-Dimers, the invention may address other analytes, providing that the sample include particles and a bi-specific agent configured to bind one of said analyte together with one of said particles. Those particles may be biological particles (i.e. Red Blood Cells), but may also be exogenous particles, such as micro-beads.

What is claimed is:

1. A method for estimating the quantity of an analyte contained in a liquid, wherein the method comprises
    introducing the liquid into a fluid chamber;
    mixing the liquid with a bi-specific reagent, the bi-specific reagent being configured for grafting on both a particle and an analyte present in the liquid;
    lighting the fluid chamber using an excitation beam emitted by a light source, the beam extending through the fluid chamber;
    acquiring at least one image using a matrix photodetector, the image being formed by radiation transmitted by the lighted fluid chamber; and
    estimating, from at least one acquired image, the quantity of said analyte in the liquid;
wherein the method further comprises:
    computing an histogram for a predetermined region of the acquired image, the histogram representing the number of pixels for each intensity value; and
    calculating an indicator for said acquired image, said indicator being dependent on the computed histogram, wherein said histogram includes at least one peak being a darkest peak corresponding to the lowest intensity values, said indicator being a function of the most represented intensity value of the darkest peak; and
    wherein the quantity of analyte is estimated according to said indicator.

2. The method according to claim 1, wherein the liquid includes blood, and the bi-specific reagent is configured for grafting on both a blood particle and an analyte present in the liquid.

3. The method according to claim 2, wherein the blood particle is a red blood cell, the bi-specific reagent being configured for grafting on both the red blood cell and the analyte.

4. The method according to claim 1, wherein the analyte is a D-dimer.

5. The method according to claim 1, wherein the estimated quantity of said analyte depends on the inverse of the most represented intensity value of the darkest peak.

6. The method according to claim 1, wherein each histogram includes two peaks, a first peak being the darkest peak corresponding to the lowest intensity values, and a second peak corresponding to intensity values greater than the intensity values of the first peak; and
    wherein the calculated indicator is a function of the number of pixels for the second peak.

7. The method according to claim 1, wherein, during the lighting step, the beam extends through the fluid chamber in a longitudinal direction; and
    wherein, during the acquisition step, the photodetector is positioned at a distance smaller than 1 cm from the fluid chamber in the longitudinal direction.

8. The method according to claim 1, wherein the beam has a surface area comprised between 5 mm$^2$ and 200 mm$^2$ in a plane perpendicular to the longitudinal direction, said plane being arranged in contact with the fluid chamber.

9. The method according to claim 1, wherein the beam directly lights the fluid chamber, and the image is formed directly by the radiation transmitted by the lighted fluid chamber, in the absence of a magnifying lens positioned between the fluid chamber and the photodetector.

10. A method for estimating the quantity of an analyte contained in a liquid, wherein the method comprises:
    introducing the liquid into a fluid chamber;
    mixing the liquid with a bi-specific reagent, the bi-specific reagent being configured for grafting on both a particle and an analyte present in the liquid;
    lighting the fluid chamber using an excitation beam emitted by a light source, the beam extending through the fluid chamber;
    acquiring at least one image using a matrix photodetector, the image being formed by radiation transmitted by the lighted fluid chamber;
    estimating, from at least one acquired image, the quantity of said analyte in the liquid;
wherein the method further comprises:
    computing an histogram for a predetermined region of the acquired image, the histogram representing the number of pixels for each intensity value;
    calculating an indicator for said acquired image, said indicator being dependent on the computed histogram, wherein said histogram includes two peaks, a first peak being a darkest peak corresponding to the lowest intensity values, and a second peak corresponding to intensity values greater than the intensity values of the first peak, said indicator being a function of the number of pixels for the second peak;

and wherein the quantity of analyte is estimated according to said indicator.

11. The method according to claim 10, wherein the liquid includes blood, and the bi-specific reagent is configured for grafting on both a blood particle and an analyte present in the liquid.

12. The method according to claim 10, wherein the blood particle is a red blood cell, the bi-specific reagent being configured for grafting on both the red blood cell and the analyte.

13. The method according to claim 10, wherein the analyte is a D-dimer.

14. The method according to claim 10, wherein, during the lighting step, the beam extends through the fluid chamber in a longitudinal direction; and wherein, during the acquisition step, the photodetector is positioned at a distance smaller than 1 cm from the fluid chamber in the longitudinal direction.

15. The method according to claim 10, wherein the beam has a surface area comprised between 5 mm$^2$ and 200 mm$^2$ in a plane perpendicular to the longitudinal direction, said plane being arranged in contact with the fluid chamber.

16. The method according to claim 10, wherein the beam directly lights the fluid chamber, and the image is formed directly by the radiation transmitted by the lighted fluid chamber, in the absence of a magnifying lens positioned between the fluid chamber and the photodetector.

* * * * *